(12) United States Patent
Kelley

(10) Patent No.: US 7,491,701 B2
(45) Date of Patent: Feb. 17, 2009

(54) PEPTIDES THAT BIND TO HSP90 PROTEINS

(75) Inventor: Philip M. Kelley, Omaha, NE (US)

(73) Assignee: Boys Town National Research Hospital, Omaha, NE (US)

( * ) Notice: Subject to any disclaimer, the term of this patent is extended or adjusted under 35 U.S.C. 154(b) by 573 days.

(21) Appl. No.: 11/034,404

(22) Filed: Jan. 12, 2005

(65) Prior Publication Data

US 2005/0209158 A1 Sep. 22, 2005

Related U.S. Application Data

(60) Provisional application No. 60/591,682, filed on Jul. 28, 2004, provisional application No. 60/539,765, filed on Jan. 27, 2004.

(51) Int. Cl.
*A61K 8/00* (2006.01)
*A61K 8/18* (2006.01)
*A61K 8/30* (2006.01)
*A61K 9/00* (2006.01)
*C07K 7/00* (2006.01)
*C07K 9/00* (2006.01)
*C07K 14/00* (2006.01)
*C07K 14/47* (2006.01)

(52) U.S. Cl. ............... 514/14; 514/2; 514/12; 514/13; 514/15; 514/16; 530/300; 530/324; 530/325; 530/326; 530/327; 530/328; 530/329

(58) Field of Classification Search .............. None
See application file for complete search history.

(56) References Cited

U.S. PATENT DOCUMENTS

| | | | |
|---|---|---|---|
| 3,595,955 | A | 7/1971 | De Boer et al. |
| 4,261,989 | A | 4/1981 | Sasaki et al. |
| 4,938,949 | A | 7/1990 | Borch et al. |
| 5,387,584 | A | 2/1995 | Schnur |
| 5,519,116 | A | 5/1996 | Wagner et al. |
| 5,595,887 | A | 1/1997 | Coolidge et al. |
| 5,932,566 | A | 8/1999 | Schnur et al. |
| 6,245,759 | B1 | 6/2001 | Bilodeau et al. |
| 6,306,874 | B1 | 10/2001 | Fraley et al. |
| 6,313,138 | B1 | 11/2001 | Fraley et al. |

| | | |
|---|---|---|
| 2003/0194409 A1 | 10/2003 | Rothman et al. |

FOREIGN PATENT DOCUMENTS

| | | |
|---|---|---|
| WO | WO01/70972 A2 | 9/2001 |
| WO | WO 2005/072766 A2 | 8/2005 |
| WO | WO 2005/072766 A3 | 8/2005 |

OTHER PUBLICATIONS

Protein Purification Handbook, Amersham Biosciences, Edition AC, 2001.*
Andersson et al., "Protein Targeting to Endoplasmic Reticulum by Dilysine Signals Involves Direct Retention in Addition to Retrieval", *Journal of Biol. Chem.*, 1999; 274:15080-15084.
Bansal et al., "Dysferlin and the plasma membrane repair in muscular dystrophy," *Trends in Cell Biology*, Apr. 2004; 14(4):206-213.
Bi et al., "Calcium-regulated Exocytosis is Required for Cell Membrance Resealing," *Journal of Cell Biol.*, Dec. 1995; 131(6):1747-1758.
Bosch et al., "Prevalence of Human Papillomavirus in Cervical Cancer: a Worldwide Perspective," *Journal of the National Cancer Institute*, Jun. 1995; 87(11):796-802.
Buchner, "Hsp90 & Co.—a holding for folding," *TIBS*, Apr. 1999; 24:136-141.
Bushby, "Dysferlin and muscular dystrophy," *Acta Neurol. Belg.*, 2002; 100:142-145.
Caplan, "Hsp90's secrets unfold: new insights from structural and functional studies," *Trends in Cell. Biol.*, Jul. 1999; 9:262-268.
Chang et al., "Hsc70 is required for endocytosis and clathrin function in *Drosphila*," *J. Cell. Biol.*, 2002; 159(3):477-487.
Chen et al., "Hypoxia increases Hsp90 binding to eNOS via P13K-Akt in porcine coronary artery endothelium," *Lab. Invest.*, 2004; 84:182-190.
Citri et al., "Drug-induced ubiquitylation and degradation of ErbB receptor tyrosine kinases: implications for cancer therapy," *EMBO Journal*, 2002; 21(10):2407-2417.
Dai et al., "Physical Interaction of Mammalian CDC37 with CDK4," *J. Biol. Chem.*, 1996; 271:22030-22034.
Detrait et al., "Axolemmal Repair Requires Proteins That Mediate Synaptic Vesicle Fusion," *J. Neurobiol.*, 2000; 44:382-391.
Draper et al., "Use of Aminoglycoside Antibiotics and Related Compounds to Study ADP-Riboslation Factor (ARF)/Coatomer Function in Golgi Traffic", *Methods in Enzymology*, 2001; 329:372-379.

(Continued)

*Primary Examiner*—Anish Gupta
*Assistant Examiner*—Julie Ha
(74) *Attorney, Agent, or Firm*—Mueting, Raasch & Gebhardt, P.A.

(57) ABSTRACT

YSLPGYMVKKLLGA (SEQ ID NO:1) and its active analogs, compositions, and methods of use.

22 Claims, 7 Drawing Sheets

OTHER PUBLICATIONS

Dyson, "The regulation of E2F by pRB-family proteins," *Genes Dev.*, 1998; 12:2245-2262.

Egan et al., "Binding of the *Rb1* protein to E1A products is required for adenovirus transformation," *Oncogene*, 1989; 4:383-388.

Goldberg, "Decoding of sorting signals by Coatomer through a GTPase Switch in the COPI Coat Complex", *Cell.*, Mar. 17, 2000; 100(6):671-679.

Grenert et al., "The Amino-terminal Domain of Heat Shock Protein 90 (hsp90) That Binds Geldanamycin Is an ATP/ADP Switch Domain That Regulates hsp90 Conformation," *J. Biol. Chem.*, 1997; 272(38):23843-23850.

Hartmann et al., "Effects of the Tyrosine-Kinase Inhibitor Geldanamycin on Ligand-Induced HER-2/NEU Activation, Receptor Expression and Proliferation of HER-2-Positive Malignant Cell Lines," *Int. J. Cancer*, 1997; 70:221-229.

Higashiyama et al., "Retinoblastoma Protein Expression in Lung Cancer: An Immunohistochemical Analysis," *Oncology*, 1994; 51:544-551.

Hudson et al., "Interaction of coatomer with aminoglycoside antibiotics; evidence that coatomer has at least two dilysine binding sites", *Mol. Biol. Cell*, Oct. 8, 1997; 8(10):1901-10.

Hu et al., "Hsp90 is required for the activity of a hepatitis B virus reverse transcriptase," *Proc Natl Acad Sci USA*, Feb. 1996; 93:1060-1064.

Ishiji, "Molecular Mechanism of Carcinogenesis by Human Papillomavirus-16," *J. Dermatol.*, 2000; 27:73-86.

Kamal et al., "A high-affinity conformation of Hsp90 cofers tumour selectivity on Hsp90 inhibitors", *Nature*, Sep. 25, 2003; 425(6956):407-410.

Kohn et al., "Colonic retinoblastoma protein and proliferation in cancer and non-cancer patients," *J. Gasroenterol. Hepatol.*, Mar. 1997; 12(3):198-203: http://gateway.ut.ovid.com/gw1/ovidweb.cgi (Apr. 29, 2005).

Kuhn-Nentwig, "Antimicrobial and cytolytic peptides of venomous arthropods", *Cell. Mol. Life Sci.*, 2003; 60:2651-2688.

Letourneur et al., "Coatomer is Essential for Retrieval of Dilysine-Tagged Proteins to the Endoplasmic Reticulum," *Cell*, Dec. 1994; 79:1199-1207.

Letunic et al., "Recent improvements to the SMART domain-based sequence annotation resource," *Nucleic Acids Res.*, 2002; 30(1):242-244.

Maloney et al., "HSP90 as a new therapeutic target for cancer therapy: the story unfolds," *Expert Opin. Biol. Ther.*, 2002; 2(1):3-24.

Mayorga et al., "Calcium-dependent Fusion Among Endosomes," *J. Biol. Chem.*, Dec. 1994; 269(49):30927-30934.

Miller et al., "Depletion of the *erb*B-2 Gene Product p185 by Benzoquinoid Ansamycins," *Cancer Res.*, May 1994; 54:2724-2730.

Mimnaugh et al., "Polyubiquitination and Proteasomal Degradation of the p185[c-erbB-2] Receptor Protein-tyrosine Kinase Induced by Geldanamycin," *J. Biol. Chem.*, Sep. 1996; 271(37):22796-22801.

Miyake et al., "Vesicle Accumulation and Exocytosis at Sites of Plasma Membrane Disruption," *J. Cell. Biol.*, 1996; 131(6):1737-1745.

Muise-Helmericks et al., "Cyclin D Expression Is Controlled Post-transcriptionally via a Phosphatidylinositol 3-Kinase/Akt-dependent Pathway," *J. Biol. Chem.*, Nov. 1998; 273(45):29864-29872.

Munster, "Modulation of Hsp90 Function by Ansamycins Sensitizes Breast Cancer Cells to Chemotherapy-induced Apoptosis in an RB- and Schedule-dependent Manner," *Clinical Cancer Research*, Aug. 2001; 7:2228-2236.

Neckers, "Development of Small Molecule Hsp90 Inhibitors: Utilizing Both Forward and Reverse Chemical Genomics for Drug Identification," *Cur. Med. Chem.* 2003; 10:733-739.

Newmyer et al., "Dominant-interfering Hsc70 Mutants Disrupt Multiple Stages of the Clathrin-coated Vesicle Cycle In Vivo," *J. Cell. Biol.*, 2001; 152(3):607-620.

Panaretou et al., "ATP binding and hydrolysis are essential to the function of the Hsp90 molecular chaperone in vivo," *EMBO J.*, 17(16):4829-4836.

Pratt et al., "Regulation of Signaling Protein Function and Trafficking by the hsp90/hsp70-Based Chaperone Machinery," *Soc. for Exp. Biol. Med.*, 2003; 228:111-133.

Presti et al., "Expression of the Retinoblastoma Gene Product in Renal Tumors," *Anticancer Res.*, 1996; 16:549-556.

Prodromou et al., "Identification and Structural Characterization of the ATP/ADP-Binding Site in the Hsp90 Molecular Chaperone," *Cell*, 1997; 90;65-75.

Rygaard et al., "Abnormalities in Structure and Expression of the Retinoblastoma Gene in Small Cell Lung Cancer Cell Lines and Xenografts in Nude Mice," *Cancer Res.*, Sep. 1990; 50:5312-5317.

Ryo et al., "Prolyl isomerase Pin 1: a catalyst for oncogenesis and a potential therapeutic target in cancer," *J Cell Sci.*, 2003; 116:773-783.

Sasagawa et al., "Serological Responses to Human Papillomavirus Type 6 and 16 Virus-Like Particles in Patients with Cervical Neoplastic Lesions," *Clinical Diag. Lab. Immunol*, 1996; 3(4):403-410.

Scheffner et al., "The E6 Oncoprotein Encoded by Human Papillomavirus Types 16 and 18 Promotes the Degradation of p53," *Cell*, Dec. 1990, 63:1129-1136.

Scheibel et al., "The charged region of Hsp90 modulates the function of the N-terminal domain," *Proc. Natl. Acad. Sci. USA*, 1999; 96:1297-1302.

Schneider et al., "Pharmacologic shifting of a balance between protein refolding and degradation mediated by Hsp90," *Proc. Natl. Acad. Sci. USA*, 1996; 93:14536-14541.

Schnur et al., "Inhibition of the Oncogene Product p185[erbB-2] in Vitro and in Vivo by Geldanamycin and Dihydrogeldanamycin Derivatives," *J. Med. Chem.*, 1995; 38:3806-3812.

Schulte et al., "Disruption of the Raf-1-Hsp90 Molecular Complex Results in Destabilization of Raf-1 and Loss of Raf-1-Ras Association," *J. Biol. Chem.*, 1995; 270(41):24585-24588.

Schulte et al., "Geldanamycin-Induced Destabilization of Raf-1 Involves the Proteasome," *Biochem. Biophys. Res. Commun.*, 1997; 239:655-659.

Schultz et al., "SMART, a simple modular architecture research tool: Identification of signaling domains," *Proc. Natl. Acad. Sci. USA*, 1998; 95:5857-5864.

Segnitz et al., "The Function of Steroid Hormone Receptors Is Inhibited by the hsp90-specific Compound Geldanamycin," *J. Biol. Chem.*, 1997; 272(30):18694-18701.

Sepp-Lorenzino et al., "Herbimycin A Induces the 20 S Proteasome- and Ubiquitin-dependent Degradation of Receptor Tyrosine Kinases," *J. Biol. Chem.*, 1995; 270(28):16580-16587.

Shao et al., "Evidence that Protein Phosphatase 5 Functions To Negatively Modulate the Maturation of the Hsp90-Dependent Heme-Regulated eIF2$\alpha$ Kinase," *Biochemistry*, 2002; 41:6770-6779.

Sinclair, "Cyclic X-Ray Responses in Mammalian Cells in vitro," *Radiation Research*, 1968; 33:620-643.

Smith et al., "Progesterone Receptor Structure and Function Altered by Geldanamycin, and hsp90-Binding Agent," *Mol. Cell. Biol.*, 1995; 15(12):6804-6812.

Stebbins et al., "Crystal Structure of an Hsp90-Geldanamycin Complex: Targeting of a Protein Chaperone by an Antitumor Agent," *Cell*, 1997; 89:239-250.

Stepanova et al., "Mammalian p50$^{Cdc37}$ is a protein kinase-targeting subunit of Hsp90 that binds and stabilizes Cdk4," *Genes Dev.*, 1996; 10:1491-1502.

Su et al., "Role of calpain in hypoxic inhibition of nitric oxide synthase activity in pulmonary endothelial cells," *Am. J. Physiol. Lung Cell Mol. Physiol.*, 2000; 278:L1204-L1212.

Takumida et al., "Heat shock protein 70 delays gentamicin-induced vestibular hair cell death," *Acta Oto-Laryngologica*, 2005; 125:23-28.

Uehara et al., "—Rapid Communication—Screening of Agents Which Convert 'Transformed Morphology' of Rous Sarcoma Virus-Infected Rat Kidney Cells to 'Normal Mophology' Identification of an Active Agent as Herbimycin and its Inhibition of Intracellular *src* Kinase," *Jpn. J. Cancer Res.*, 1985; 76:672-675.

Uehara et al., "Inhibition of Transforming Activity of Tyrosine Kinase Oncogenes by Herbimycin A," *Virology*, 1988; 164:294-298.

Vasilevskaya et al., "Effects of Geldanamycin on Signaling through Activator-Protein 1 in Hypoxic HT29 Human Colon Adenocarcinoma Cells," *Cancer Res.*, 1999; 59:3935-3940.

Weinberg, "The Retinoblastoma Protein and Cell Cycle Control," *Cell*, May 1995; 81:323-330.

Whitesell et al., "Inhibition of heat shock protein HSP90-pp60[v-src] heteroprotein complex formation by benzoquinone ansamycins: Essential role for stress proteins in oncogenic transformation," *Proc. Natl. Acad. Sci. USA*, 1994; 91:8324-8328.

Winkler et al., "Requirements of the Prolyl Isomerase Pin1 for the Replication Checkpoint," *Science*, 2000; 287:1644-1647.

Workman, "Overview: Translating Hsp90 Biology into Hsp90 Drugs", *Current Cancer Drug Targets*, 2003, 3:297-300.

Yasunaga et al., "A mutation in *OTOF*, encoding otoferlin, a FER-1-like protein, causes DFNB9, a nonsyndromic form of deafness," *Nat. Genet.*, 1999; 21:363-369.

Young et al., "More than folding: localized functions of cytosolic chaperones," *Trends Biochem. Sci.*, 2003; 28(10):541-547.

Young et al., "Hsp90: a specialized but essential protein-folding tool," *J. Cell. Biol.*, 2001; 154(2):267-273.

Zalvide et al., "The J Domain of Simian Virus 40 Large T Antigen Is Required To Functionally Inactivate RB Family Proteins," *Mol. Cell. Biol.*, 1998; 18(3):1408-1415.

Zhou et al., "Phosphorylation-dependent prolyl isomerization: a novel signaling regulatory mechanism", *Cell. Mol. Life Sci.*, 1999; 56:788-806.

Bansal et al., "Defective membrane repair in dysferlin-deficient muscular dystrophy," May 8, 2003, Nature, 423:168-172.

Burrows et al., "Hsp90 Activation and Cell Cycle Regulation," Dec. 2004, Cell Cycle, 3(12):e20-e26.

Chiosis et al., "Hsp90: the vulnerable chaperone," Oct. 2004, Drug Discovery Today, 9:881-888.

Dyson et al., "The Human Papilloma Virus-16 E7 Oncoprotein Is Able to Bind to the Retinoblastoma Gene Protein," Feb. 1989, Science, 243:934-937.

Fields et al. in "Synthetic Peptides: A User's Guide: Chapter 3, Principles and Practice of Solid-Phase Peptide Synthesis," W. M. Freeman & Company, New York, N.Y., pp. 77-183 (1992).

Kamal et., "Therapeutic and diagnostic implications of Hsp90 activation," Jun. 2004, Trends in Mol. Med., 10:283-290.

McNeil et al., "Coping with the inevitable: how cells repair a torn surface membrane," May 2001, Nat. Cell Biol., 3:E124-E129.

Pratt et al., "Role of hsp90 and the hsp90-binding immunophilins in signalling protein movement," 2004, Cellular Signalling, 16:857-872.

Steinhardt et al., "Cell Membrane Resealing by a Vesicular Mechanism Similar to Neurotransmitter Release," Jan. 21, 1994, Science, 263:390-393.

Varga et al., "Non-syndromic recessive auditory neuropathy is the result of mutations in the otoferlin (*OTOF*) gene," 2003, J. Med. Genet., 40:45-50.

Wegele et al., "Hsp70 and Hsp90—a relay team for protein folding," 2004, Rev Physiol Biochem Pharmocol 151:1-44.

Yasunaga et al., "*T F* Encodes Mu tip e Long and Short Isoforms: Genetic Evidence That the Long Ones Under ie Recessive Deafness DFNB9." 2000, Am. J. Hum. Genet., 67:591-600.

Brinker et al., "Ligand Discrimination by TPR Domains," *The Journal of Biological Chemistry*, 277(22):19265-19275 (May 2002).

Hekman et al., "Isolation and identification of cyclic imide and deamidation products in heat stressed pramlintide injection drug product," Sep. 1999 *J. Pharm. Biomed. Analysis* 20(5):763-772.

Kelley et al., "In vitro synthesis of heat-shock proteins by mRNAs from chicken embryo fibroblasts," Apr. 25, 1980 *J. Biol. Chem.* 255(8):3230-3233.

Kelley et al., "A preliminary comparison of maize anaerobic and heat-shock proteins," in *Heat Shock from Human to Bacteria*, Schlesinger et al. (eds.). Cold Spring Harbor Laboratory Press: Cold Spring Harbor, New York; 1982. Title page, publishers page, and pp. 315-319.

Kelley and Schlesinger, "Antibodies to two major chicken heat shock proteins cross-react with similar proteins in widely divergent species," Mar. 1982 *Mol. Cell. Biol.* 2(3):267-274.

Kelley et al., "The genomic structure of the gene defective in Usher syndrome type Ib (MYO7A)," Feb. 15, 1997 *Genomics* 40(1):73-79.

Kelley et al., "Novel mutations in the connexin 26 gene (GJB2) that cause autosomal recessive (DFNB1) hearing loss," Apr. 1998 *Am. J. Human Genetics* 62(4):792-799. Epub Apr. 1, 2008.

Kelley et al., "Human connexin 30 (GJB6), a candidate gene for nonsyndromic hearing loss: molecular cloning, tissue-specific expression, and assignment to chromosome 13q12," Dec. 1, 1999 *Genomics* 62(2):172-176.

Kelley et al., "Connexin 26: required for normal auditory function," Apr. 2000 *Brain Res. Rev.* 32(1):184-188.

Kelley et al., "Thermally induced disintegration of the oligomeric structure of (alpha)B-crystallin mutant F28S is associated with diminished chaperone activity," Oct. 2003 *Mol. Cell. Biochem.* 252(1 &2):273-278.

Lal et al., "Purification and differential expression of enolase from maize," 1994 *Physiologia Plantrum* 91(4):587-592.

National Center for Biotechnology Information, National Library of Medicine, National Institutes of Health, GenBank Locus AF183183, Accession No. AF183183, "Mus musculus cochlear otoferlin (otof) mRNA, complete cds," [online]. Bethesda, MD [retrieved on Jul. 9, 2008]. Retrieved from the Internet: <http://www.ncbi.nlm.nih.gov/entrez/viewer.fcgi?db=nuccore&id=10119911>; 4 pgs.

National Center for Biotechnology Information, National Library of Medicine, National Institutes of Health, GenBank Locus AF183187, Accession No. AF183187, "*Homo sapiens* heart/fetal otoferlin (OTOF) mRNA, complete cds," [online]. Bethesda, MD [retrieved on Jul. 9, 2008]. Retrieved from the Internet: <http://www.ncbi.nlm.nih.gov/entrez/viewer.fcgi?db=nuccore&id=10442755>; 3 pgs.

National Center for Biotechnology Information, National Library of Medicine, National Institutes of Health, GenBank Locus AK033317, Accession No. AK033317, "Mus musculus 15 days embryo male testis cDNA, Rinken full-length enriched library, clone: 8030492G06 product: otoferlin, full insert sequence," [online]. Bethesda, MD [retrieved on Jul. 9, 2008]. Retrieved from the Internet: <http://www.ncbi.nlm.nih.gov/entrez/viewer.fcgi?db =nuccore&id=26328980>; 5 pgs.

Orten et al., "Analysis of DNA elements that modulate myosin VIIa expression in humans," Oct. 1999 *Human Mutation* 14(4):354-360.

Orten et al., "Erratum: analysis of DNA elements that modulate myosin VIIa expression in humans," Jan. 2000 *Human Mutation* 15(1):114-119.

Pieke-Dahl et al., "Genetic heterogeneity of Usher syndrome type II. Localisation to chromosome 5q," Apr. 2000 *J. Med. Genetics* 37(4):256-262.

Schlesinger et al., "Properties of three major chicken heat-shock proteins and their antibodies," in *Heat Shock from Human to Bacteria*, Schlesinger et al. (eds.). Cold Spring Harbor Laboratory Press: Cold Spring Harbor, New York; 1982. Title page, publishers page, and pp. 243-250.

Schlesinger et al., "The response of cells to heat shock," 1982 *Trends in Biochem. Sci.* 7(6):222-225.

Smith et al., "Tietz syndrome (hypopigmentation/deafness) caused by mutation of MITF," Jun. 2000 *J. Med. Genetics* 37(6):446-448.

Talebizadeh et al., "Novel mutation in the KCNQ4 gene in a large kindred with dominant progressive hearing loss," 1999 *Human Mutation* 14(6):493-501.

VanBogelen et al., "Differential induction of heat shock, SOS, and oxidation stress regulons and accumulation of nucleotides in *Escherichia coli*," Jan. 1987 *J. Bacteriol.* 169(1):26-32.

Varga et al., "OTOF mutations revealed by genetic analysis of hearing loss families including a potential temperature sensitive auditory neuropathy allele," 2006 *J. Med. Genetics* 43(7):576-581. Epub Dec. 21, 2005.

Weston et al., "Myosin VIIa mutation screening in 189 Usher syndrome type 1 patients," Nov. 1996 *Am. J. Human Genetics* 59(9):1074-1083.

\* cited by examiner

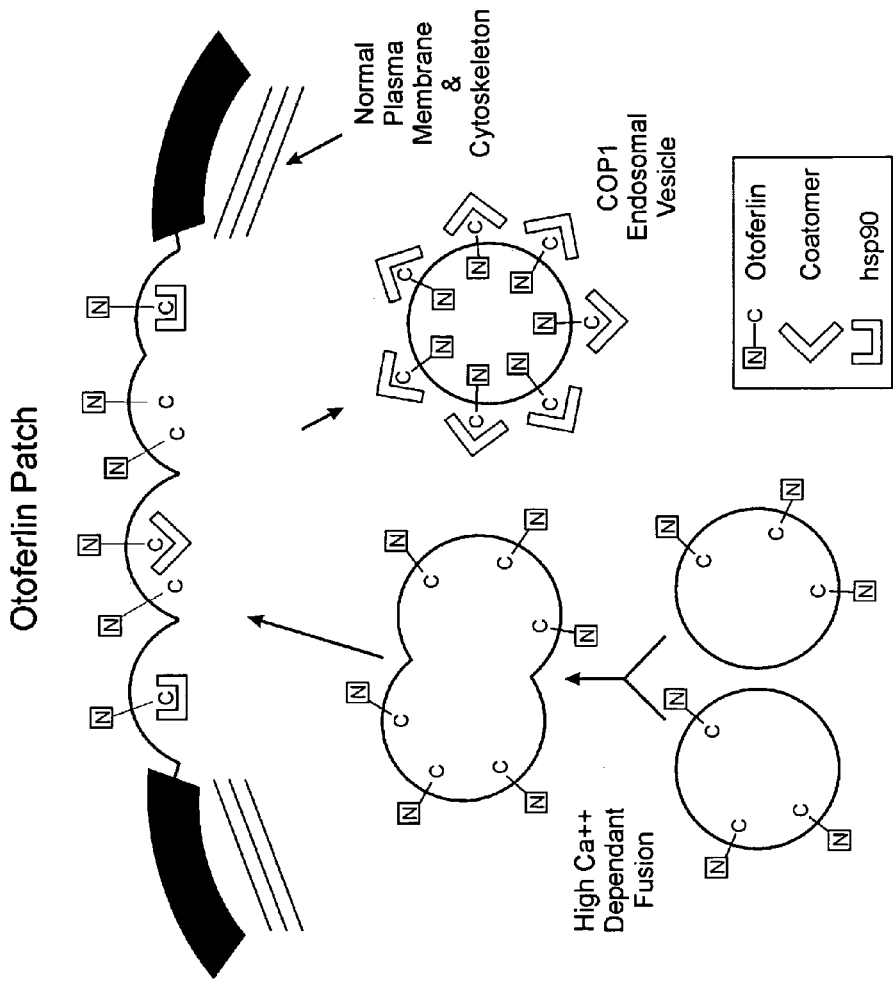

SEQUENCE LISTING

```
<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: peptide corresponding to the C-terminus of an
      otoferlin isoform

<400> SEQUENCE: 1

Tyr Ser Leu Pro Gly Tyr Met Val Lys Lys Leu Leu Gly Ala
1               5                   10

<210> SEQ ID NO 2
<211> LENGTH: 15
<212> TYPE: PRT
<213> ORGANISM: Artificial Sequence
<220> FEATURE:
<223> OTHER INFORMATION: peptide corresponding to the C-terminus of an
      otoferlin isoform

<400> SEQUENCE: 2

Cys Tyr Ser Leu Pro Gly Tyr Met Val Lys Lys Leu Leu Gly Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: peptide corresponding to the C-terminus of an
      otoferlin isoform

<400> SEQUENCE: 3

Cys Tyr Ser Leu Pro Gly Tyr Leu Ala Lys Lys Ile Leu Gly Ala
1               5                   10                  15
```

```
<210> SEQ ID NO 4
<211> LENGTH: 15
<212> TYPE: PRT
<213> ORGANISM: Artificial Sequence
<220> FEATURE:
<223> OTHER INFORMATION: peptide corresponding to the C-terminus of an
      otoferlin isoform with di-lysine replaced by di-serine

<400> SEQUENCE: 4

Cys Tyr Ser Leu Pro Gly Tyr Met Val Ser Ser Leu Leu Gly Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: peptide corresponding to the C-terminus of an
      otoferlin isoform with di-lysine replaced by di-serine

<400> SEQUENCE: 5

Cys Tyr Ser Leu Pro Gly Tyr Leu Ala Ser Ser Ile Leu Gly Ala
1               5                   10                  15
```

PEPTIDES THAT BIND TO HSP90 PROTEINS

CROSS REFERENCE TO RELATED APPLICATIONS

The present invention claims priority to U.S. Provisional Patent Application Ser. No. 60/539,765, filed on 27 Jan. 2004, and to U.S. Provisional Patent Application Ser. No. 60/591,682, filed on 28 Jul. 2004, which are incorporated herein by reference.

BACKGROUND OF THE INVENTION

The eukaryotic heat shock protein 90s (Hsp90s) are ubiquitous chaperone proteins, which bind and hydrolyze ATP. The Hsp90 family of proteins includes four known members: Hsp90-alpha and -beta, Grp94, and Trap-1. The roles of Hsp90s in cellular functions are not completely understood, but recent studies indicate that Hsp90s regulate client proteins involved in cellular signaling (Wegele et al., 2004, Rev Physiol Biochem Pharmacol 151:1-44). These client proteins include key proteins involved in signal transduction, cell cycle control, and transcriptional regulation (Burrows et al., 2004, Cell Cycle, 3:e20-e26; Pratt et al., 2004, Cellular Signalling, 16:857-872). For example, researchers have reported that Hsp90 chaperone proteins are associated with important signaling proteins, such as steroid hormone receptors and protein kinases, including many implicated in tumorigenesis, such as Raf-1, EGFR, v-Src family kinases, Cdk4, and ErbB-2 (Buchner, 1999, TIBS, 24:136-141; Stepanova et al., 1996, Genes Dev., 10:1491-1502; Dai et al., 1996, J. Biol. Chem., 271:22030-22034).

In vivo and in vitro studies indicate that without the aid of co-chaperones, Hsp90is unable to fold or activate proteins. For steroid receptor conformation and association in vitro, Hsp90 requires Hsp70 and p60/Hop/Sti1 (Caplan, 1999, Trends in Cell Biol., 9:262-268). In vivo Hsp90 may interact with Hsp70and its co-chaperones. Other co-chaperones associated with Hsp90s in higher eukaryotes include Hip, Hsp40/Hdj2/Hsj1, Immunophilins, p23, and p50 (Caplan, 1999, Trends in Cell. Biol., 9:262-268). The activation of Hsp90requires both the association with co-chaperones and ATP hydrolysis by Hsp90. Inhibition of Hsp90ATPase activity has proven an effective means to disrupt Hsp90 activity and consequently the many signaling pathways that it regulates including cell cycle pathways required for tumor growth (Kamal et., 2004, Trends in Mol. Med., 10:283-290). Inhibition of Hsp90activity has become an important target in the development of effective cancer therapy (Maloney and Workman, 2002, Expert Opin. Biol. Ther., 2:3-24; Neckers, 2003, Cur. Med. Chem. 10:733-739). While the ATPase activity of Hsp90 is the most studied target, the chaperone has many other vulnerable points (Chiosis et al., 2004, Drug Discovery Today, 9:881-888).

Ansamycin antibiotics are natural products derived from *Streptomyces hygroscopicus* that have profound effects on eukaryotic cells. Many ansamycins, such as herbimycin A (HA) and geldanamycin (GM), bind tightly to a pocket in the HSP90 protein (Stebbins et al., 1997, Cell, 89:239-250). The binding of ansamycins to Hsp90 has been reported to inhibit protein refolding and to cause the proteasome dependent degradation of a select group of cellular proteins (Sepp-Lorenzino et al., 1995, J. Biol. Chem., 270:16580-16587; Whitesell et al., 1994, Proc. Natl. Acad. Sci. USA, 91:8324-8328).

The ansamycins were originally isolated on the basis of their ability to revert v-src transformed fibroblasts (Uehara et al., 1985, Jpn. J. Cancer Res., 76:672-675). Subsequently, they were said to have antiproliferative effects on cells transformed with a number of oncogenes, particularly those encoding tyrosine kinases (Uehara et al., 1988, Virology, 164:294-298). Inhibition of cell growth is associated with apoptosis and, in certain cellular systems, with induction of differentiation (Vasilevskaya et al., 1999, Cancer Res., 59:3935-3940).

The use of ansamycins as anticancer agents are described in U.S. Pat. Nos. 4,261,989, 5,387,584, and 5,932,566. The preparation of the ansamycin, geldanamycin, is described in U.S. Pat. No. 3,595,955.

The ansamycin-binding pocket in the N-terminus of Hsp90 is highly conserved and has weak homology to the ATP-binding site of DNA gyrase (Stebbins et al., 1997, Cell, 89:239-250; Grenert et al., 1997, J. Biol. Chem., 272:23843-23850). This pocket has been reported to bind ATP and ADP with low affinity and to have weak ATPase activity (Prodromou et al., 1997, Cell, 90:65-75; Panaretou et al., 1998, EMBO J., 17:4829-4836). In vitro and in vivo studies are said to indicate that occupancy of the pocket by ansamycins alters Hsp90 function and inhibits protein refolding. At high concentrations, ansamycins have been reported to prevent binding of protein substrates to Hsp90 (Scheibel et al., 1999, Proc. Natl. Acad. Sci. USA, 96:1297-1302; Schulte et al., 1995, J. Biol. Chem., 270:24585-24588; Whitesell et al., 1994, Proc. Natl. Acad. Sci. USA, 91:8324-8328). Alternatively, they have also been reported to inhibit the ATP-dependent release of chaperone-associated protein substrates (Schneider et al., 1996, Proc. Nati. Acad. Sci. USA, 93:14536-14541; Sepp-Lorenzinoet al., 1995, J. Biol. Chem., 270:16580-16587). In both models, the unfolded substrates are said to be degraded by a ubiquitin-dependent process in the proteasome (Scheibel et al., 1999, Proc. Nati. Acad. Sci. USA, 96:1297-1302; and Sepp-Lorenzino et al., 1995, J. Biol. Chem., 270:16580-16587).

In both tumor and nontransformed cells, binding of ansamycins to Hsp90 has been reported to result in the degradation of a subset of signaling regulators. These include Raf (Schulte et al., 1997, Biochem. Biophys. Res. Commun., 239:655-659; Schulte et al., 1995, J. Biol. Chem., 270:24585-24588), nuclear steroid receptors (Segnitz, 1997, J. Biol. Chem., 272:18694-18701; Smith et al., 1995, Mol. Cell. Biol., 15:6804-6812), v-src (Whitesell et al., 1994, Proc. Natl. Acad. Sci. USA, 91:8324-8328) and certain transmembrane tyrosine kinases (Sepp-Lorenzino et al., 1995, J. Biol. Chem., 270:16580-16587) such as EGF receptor (EGFR) and Her2/Neu (Hartmann et al., 1997, Int. J. Cancer, 70:221-229; Miller et al., 1994, Cancer Res., 54:2724-2730; Mimnaugh et al., 1996, J. Biol. Chem., 271:22796-22801; Schnur et al., 1995, J. Med. Chem., 38:3806-3812). The ansamycin-induced loss of these proteins is said to lead to the selective disruption of certain regulatory pathways and results in growth arrest at specific phases of the cell cycle (Muise-Heimericks et al., 1998, J. Biol. Chem., 273:29864-29872).

Geldanamycin is a benzoquinone ansamycin polyketide isolated from *Streptomyces hygroscopicus* var. *geldanus*. Although originally discovered by screening microbial extracts for antibacterial and antiviral activity, geldanamycin was later found to be cytotoxic to certain tumor cells in vitro and to reverse the morphology of cells transformed by the Rous sarcoma virus to a normal state.

Geldanamycin's nanomolar potency and apparent specificity for aberrant protein kinase dependent tumor cells, as well as the discovery that its primary target in mammalian cells is the ubiquitous Hsp90 protein chaperone, have stimulated interest in the development of this anti-cancer drug.

However, the association of hepatotoxicity with the administration of geldanamycin led to its withdrawal from Phase I clinical trials. As with several other promising anticancer agents, geldanamycin also has poor water solubility that makes it difficult to deliver in effective doses.

More recently, attention has focused on 17-amino derivatives of geldanamycin, in particular 17-(allylamino)-17-desmethoxygeldanamycin (17-AAG), that show reduced hepatotoxicity while maintaining Hsp90 binding. Certain 17-amino derivatives of geldanamycin, 11-oxogeldanamycin, and 5,6-dihydrogeldanamycin, are disclosed in U.S. Pat. Nos. 4,261,989, 5,387,584, and 5,932,566. Like geldanamycin, 17-AAG has limited aqueous solubility.

Treatment of cancer cells with geldanamycin or 17-AAG causes a retinoblastoma protein-dependent $G_1$ block, mediated by down-regulation of the induction pathways for cyclin D-cyclin dependent cdk4 and cdk6 protein kinase activity. Cell cycle arrest is followed by differentiation and apoptosis. $G_1$ progression is unaffected by geldanamycin or 17-AAG in cells with mutated retinoblastoma protein; these cells undergo cell cycle arrest after mitosis, again followed by apoptosis.

The mechanism of action of benzoquinone ansamycins appears to be via binding to Hsp90 and subsequent degradation of Hsp90-associated client proteins. Among the most sensitive client protein targets of the benzoquinone ansamycins are the Her kinases (also known as ErbB), Raf, Met tyrosine kinase, and the steroid receptors. Hsp90 is also involved in the cellular response to stress, including heat, radiation, and toxins. Certain benzoquinone ansamycins, such as 17-AAG, have thus been studied to determine their interaction with cytotoxins that do not target Hsp90 client proteins.

U.S. Pat. Nos. 6,245,759, 6,306,874, and 6,313,138, disclose compositions comprising certain tyrosine kinase inhibitors together with 17-AAG and methods for treating cancer with such compositions. Munster, 2001, Clinical Cancer Research, 7:2228-2236, discloses that 17-AAG sensitizes cells in culture to the cytotoxic effects of paclitaxel and doxorubicin, and that the sensitization towards paclitaxel by 17-AAG is schedule-dependent in retinoblastoma protein-producing cells due to the action of these two drugs at different stages of the cell cycle. Treatment of cells with a combination of paclitaxel and 17-AAG is reported to give synergistic apoptosis, while pretreatment of cells with 17-AAG followed by treatment with paclitaxel is reported to result in abrogation of apoptosis. Treatment of cells with paclitaxel followed by treatment with 17-AAG 4 hours later is reported to show a synergistic effect similar to coincident treatment. Citri et al., 2002, EMBO Journal, 21:2407-2417, discloses an additive effect upon co-administration of geldanamycin and an irreversible protein kinase inhibitor, CI-1033, on growth of ErbB2-expressing cancer cells in vitro.

As can be seen from this discussion, inhibitors of the ATPase activity of Hsp90, such as geldanamycin and radicicol, have significant activity and a broad range as anti-tumor drugs. Considerable resources are being directed to develop derivatives of these drugs that are stable and do not have objectionable side effects. Some of these drugs are currently in clinical trials. The development of Hsp90 ATPase inhibitors without significant side effects is an important goal of cutting edge cancer research.

Thus, what is needed is the discovery of additional agents that interact with Hsp90 and that can be used in the treatment of conditions, particularly various cancers or other cell proliferative disorders, as well as viral infections.

SUMMARY OF THE INVENTION

The invention is directed to the isolated peptide (i.e., polypeptide) having (preferably consisting essentially of, and more preferably consisting of) the sequence YSLPGYMVKKLLGA (SEQ ID NO:1) or its active analogs. The isolated peptides of the invention bind to at least one member of the Hsp90 class of proteins and preferably inhibit the ability of the Hsp90 protein (i.e., the member of the Hsp90 class of proteins) to regulate one or more client proteins (e.g., the amount and/or activity).

The function of Hsp90 proteins is to regulate client proteins so that they can perform specific functions. This is accomplished by assembling a complex of proteins including co-chaperones that associate with the client protein. Part of the assembly of this activated form of the Hsp90 protein requires ATP hydrolysis, ATPase activity associated with Hsp90. Thus, regulating a client protein, herein, means regulating the amount (increased or decreased) and/or activity (e.g., kinase activity, transcription activity) of such protein.

This discovery of a peptide that binds to at least one member of the Hsp90 class of proteins (preferably, in a very specific fashion) makes it a candidate Hsp90 ATPase inhibitor, and provides a novel class of Hsp90 ATPase inhibitors that can be used as a new front to defeat cancer, for example.

The peptide YSLPGYMVKKLLGA (SEQ ID NO:1) is based on the 14 amino acids of the C-terminus of the human/mouse otoferlin isoform found in the cochlea (form including exon 48 but excluding exon 47). A shorter (e.g., as short as 7 amino acids) or longer (e.g., up to 30 amino acids) form of this peptide sequence may be active.

Herein, the term "Hsp90" refers to the family of Hsp90 heat shock proteins. Thus, this term encompasses Hsp90-alpha, Hsp90-beta, Grp94, and Trap-1. The Hsp90 heat shock proteins each possess a characteristic pocket located near the N-terminal end of the protein to which ATP and ADP bind. This is the same pocket which has been shown to bind to ansamycin antibiotics. This pocket is referred to herein as "the N-terminal pocket of Hsp90." Thus, preferred peptides of the invention bind to the N-terminal pocket of an Hsp90 protein (although they may also bind to other portions of the Hsp90 protein or to a co-chaperone). The preferred peptides of the invention bind the Hsp90-alpha protein in a manner that inhibits its ability to regulate Hsp90 client proteins (typically, by inhibiting its activation).

The present invention also provides a method for treating a subject for a disorder that is associated with cells that are Rb negative or Rb deficient. The method includes administering to the subject an effective amount of a composition including a polypeptide of claim 1. Preferably, the peptide has an $IC_{50}$ against Rb negative or Rb deficient cells that is at least 5-fold lower than the $IC_{50}$ against similar cells that are not Rb negative or Rb deficient. Disorders that have associated therewith Rb negative or Rb deficient cells include cell proliferative disorders and viral infections, for example.

The present invention provides a method for treating (e.g., preventing and/or reversing) a cell proliferative disorder (e.g., tumorogenesis) in a subject. The method includes administering to the subject an effective amount of a composition including a polypeptide described herein.

The present invention provides a method for treating (e.g., preventing and/or reversing) tumorigenesis in a subject. The method includes administering to the subject an effective amount of a composition including a polypeptide described herein.

The present invention also provides a method for treating (e.g., preventing and/or reversing) viral infection in a subject.

The method includes administering to the subject an effective amount of a composition including a polypeptide described herein.

This invention provides an active agent for treating disorders (e.g., diseases) where Hsp90 plays a role in the progression of the disorder (for example, by regulating a client protein where increased or decreased amounts of, or increased or decreased activity of, the client protein is responsible for the disorder). The method includes administering to the subject an effective amount of a composition including a polypeptide described herein.

These peptide inhibitors can be used in vitro or in vivo, including internal and external use in animals, including mammals such as humans. They can be used for preventative (i.e., prophylactic) treatments or for therapeutic treatments.

As used herein, "a" or "an" means one or more (or at least one), such that combinations of active agents, for example, can be used in the compositions and methods of the invention. Thus, a composition that includes "a" polypeptide refers to a composition that includes one or more polypeptides. Herein, a "composition" could include just the peptide.

The terms "comprises" and variations thereof do not have a limiting meaning where these terms appear in the description and claims.

The terms "polypeptide" and "peptide" are used interchangeably herein to refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted.

The following abbreviations are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 1A Coomassie stained gel, FIG. 1B Western analysis of an identical gel with antibody to beta-COP. MW=molecular weight markers, Total=13,200 rpm supernatant loaded onto column matrix. E47=sample eluted from OTOF CTERM E47 column matrix. BC1=672 BC1, E48=OTOF CTERM E48, CC1=670 CC1. Brain extracts were made in a Potter-Elvehjem Teflon glass homogenizer using 1 ml/100 mg tissue of TNGD (50 mM TRIS 7.5, 75 mM NaCl, 10 mM EGTA, 2 mM EDTA) plus protease inhibitor 10 ul/ml (Sigma P8340). Protein extracts were absorbed to four Sulfolink-peptide affinity matrices and washed four times with TNGD. The column matrix was transferred to PCR tubes and made 1× with SDS buffer (Pierce Cat. No. 39001) and heated at 95° C. for 5 minutes. Samples were separated on a 4-20% polyacrylamide gel. E47 peptide corresponds to otoferlin exon 47 C-terminal. E48 peptide corresponds to otoferlin exon 48 C-terminal. BC1 and CC1 peptides are specific controls for E47 and E48 respectively where a di-serine replaces di-lysine. Antibody to beta-COP (Ocogene cat # PC175) was used at a dilution of 1:1500.

FIG. 7. Proposed otoferlin triggered membrane repair. High calcium concentration initiates promiscuous vesicle fusion forming larger vesicles that plug the membrane rift. The repaired membrane patch is "marked" for endosomal recovery by a COPI endosomal vesicle recycling pathway regulated by Hsp90 as the cell repairs the wounded area membrane and sub-plasma membrane cytoskeletal structure.

DETAILED DESCRIPTION OF ILLUSTRATIVE EMBODIMENTS OF THE INVENTION

Figure 1A:
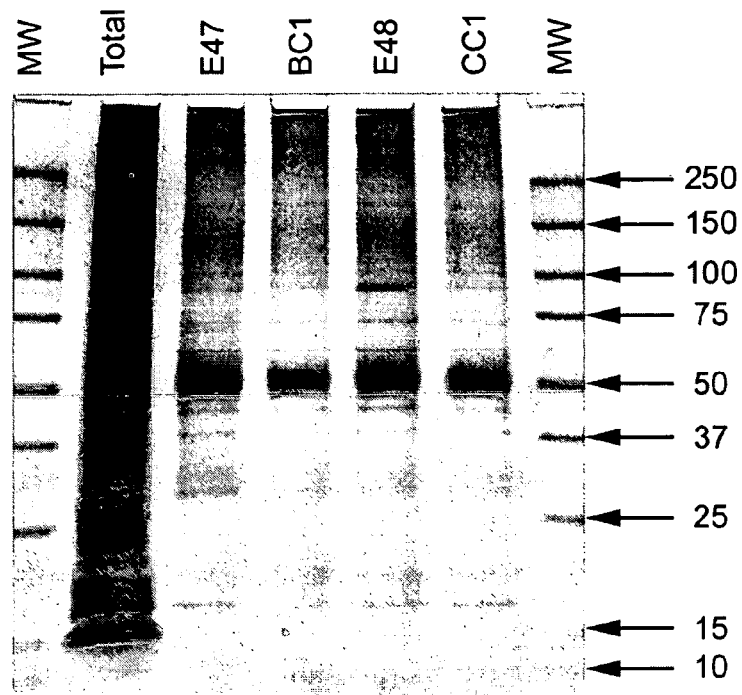
FIGS. 1A AND 1B. Binding of mouse brain protein extract to otoferlin C-terminus peptide columns.

The present invention is directed to isolated peptides that have the sequence YSLPGYMVKKLLGA (SEQ ID NO:1) or active analogs thereof.

The present application makes use of peptides that bind to at least one Hsp90 protein (preferably, the N-terminal pocket of at least one Hsp90 protein (particularly Hsp90-alpha) and optionally another Hsp90 binding site or co-chaperone) in a manner that preferably results in an inhibition of its ability to regulate one or more client proteins (e.g., the amount of and/or the activity of a client protein).

The peptide YSLPGYMVKKLLGA (SEQ ID NO:1) is based on the 14 amino acids of the C-terminus of the human/mouse otoferlin isoform found in the cochlear (form including exon 48 but excluding exon 47). Otoferlin is expressed in several types of tissue but predominantly in the brain, heart, and the inner hair cells. Only an auditory phenotype is known to be associated with mutations that inactivate otoferlin in humans. Mutations in the otoferlin gene cause auditory neuropathy/dyssynchrony and profound hearing loss (Yasunaga, 1999, Nat. Genet., 21:363-9; Yasunaga et al., Am. J. Hum. Genet., 67:591-600; Varga, 2003, J. Med. Genet., 40:45-50). Such mutations may be responsible for as much as 2% of all childhood hearing loss.

The polypeptides of this invention can be added to cells in culture or used to treat subjects, such as mammals. Where the polypeptides are used to treat a subject, the polypeptides are preferably combined in a pharmaceutical composition with a pharmaceutically acceptable carrier, such as a larger molecule to promote polypeptide stability or a pharmaceutically acceptable buffer that serves as a carrier for the polypeptide.

Treatment can be prophylactic or therapeutic. Thus, treatment can be initiated before, during, or after the development of the condition (e.g., viral infection or cancer). As such, the phrases "treating," "inhibiting," "effective to inhibit," and the like includes both prophylactic and therapeutic treatment (i.e., prevention and/or reversal of the condition).

The peptides of the invention include the sequence YSLPGYMVKKLLGA (SEQ ID NO:1) or active analogs thereof. Peptides of the invention can be shorter (e.g., as short as 7 amino acids) or longer (e.g., up to 30 amino acids) than the sequence YSLPGYMVKKLLGA (SEQ ID NO:1). Preferably, however, peptides of the invention are no shorter than 12 amino acids, and more preferably, no shorter than 14 amino acids. Such short amino acid segments would be fragments of YSLPGYMVKKLLGA (SEQ ID NO:1) and hence, contiguous amino acids from this 14 amino acid sequence. As used in this context, an "active analog" of YSLPGYMVKKLLGA (SEQ ID NO:1) binds to at least one member of the Hsp90 class of proteins and alters its ability to regulate one or more client proteins. An Hsp90 protein regulates client proteins by binding them and stabilizing them so it regulates the amount of the client protein and it also binds to them and regulates client protein activity (such as kinase activity, transcription activity).

Peptides of the invention, whether they include the sequence YSLPGYMVKKLLGA (SEQ ID NO:1) or its active analogs, bind to at least one member of the Hsp90 class of proteins (e.g., Hsp90-alpha, and Hsp90-beta, Grp94, and Trap-1), preferably to Hsp90-alpha. Preferably, peptides of the invention bind to the N-terminal pocket of an Hsp90 protein (although they may also bind to other portions of the protein and/or to co-chaperones). Upon such binding, peptides of the invention preferably inhibit the ability of the Hsp90 protein to regulate one or more client proteins (typically, it is believed, by inhibiting the activation of Hsp90). Hsp90 client proteins are primarily involved in cellular signaling (Pratt, 2004, Cellular Signalling, 16:857-872; Wegele et al., 2004, Rev. Physiol. Biochem. Pharmacol., 151:1-44). Transcription factors and kinases make up the largest class of proteins that are regulated by Hsp90 (Table 1).

TABLE 1

Hsp90 client proteins (Wegele et al., 2004, Rev. Physiol. Biochem. Pharmacol., 151: 1-44)

| FUNCTIONAL CLASS | PROTEIN NAME |
| --- | --- |
| Transcription | Androgen receptor |
| | Aryl hydrocarbon (Ah) receptor |
| | Ecdysone receptor |
| | Estrogen receptor |
| | Glucocorticoid receptor |
| | Heme activator protein (Hap1) |
| | HSF-1 |
| | Hypoxia-inducible factor-1a |
| | Mineralocorticoid receptor |
| | MTG8 myeloid leukemia protein |
| | p53 |
| | Progesterone receptor |
| | Retinoid receptor |
| | Sim |
| | SV40 large T antigen |
| | Tumor promotor-specific binding protein |
| | v-erbA |
| Polymerases | Telomerase |
| | Hepatitis B virus reverse transcriptase |
| | DNA-polymerase a |
| Kinases | 3-Phosphoinositide-dependent kinase-1 |
| | Akt |
| | Bcr-Abl |
| | Calmodulin-regulated eEF-2 kinase |
| | Casein kinase II |
| | Cdc2 |
| | Cdk4 |
| | Cdk6 |
| | Cdk9 |
| | c-Mos |
| | Epidermal growth factor receptor |
| | ErbB2 |
| | Focal adhesion kinase |
| | Hck |
| | Heme-regulated eIF-2a kinase |
| | Insulin receptor |
| | Insulin-like growth factor receptor |
| | Kinase suppressor of ras (KSR) |
| | Lymphoid cell kinase p56lck |
| | MAK-related kinase |
| | Male germ cell-associated kinase MAK |
| | MEK (MAP kinase kinase) |
| | Mik1 |
| | Mitogen-activated protein kinase MOK |
| | Phosphatidylinositol 4-kinase |
| | Pim-1 |
| | PKR |

TABLE 1-continued

Hsp90 client proteins (Wegele et al., 2004, Rev. Physiol. Biochem. Pharmacol., 151: 1-44)

| FUNCTIONAL CLASS | PROTEIN NAME |
|---|---|
| | Platelet-derived growth factor receptor |
| | Polo mitotic kinase |
| | Raf family kinases: v-Raf, c-Raf, B-Raf, Gag-Mil, Ste11 |
| | Receptor-interacting protein (RIP) |
| | Sevenless PTK |
| | Swe1 |
| | Translation initiation factor kinase Gcn2 |
| | Tropomyosin related kinase B (trkB) |
| | v-fes |
| | v-fps |
| | v-fgr, c-fgr |
| | v-Src, c-Src |
| | v-yes |
| | Wee1 |
| Others | Actin |
| | Apaf-1 |
| | Apoprotein B |
| | Atrial natriuretic peptide receptor |
| | Calponin |
| | Centrin/centrosome |
| | Cna2 (catalytic subunit of calcineurin) |
| | CFTR |
| | Endothelial NOS |
| | Fanconi anemia group C protein |
| | G protein bg |
| | Ga0 |
| | Ga12 |
| | Guanylate cyclase (b-subunit) |
| | HETE binding complex |
| | Inducible NOS |
| | Lysosomal membrane |
| | Macrophage scavenger receptor |
| | Aminoacyl t-RNA synthetase |
| | Mdm2 |
| | Myosin |
| | Neuronal NOS |
| | Pancreatic bile salt-dependent lipase |
| | Erythrocyte membrane protein |
| | Protease-activated receptor 1 (PAR-1) |
| | Proteasome |
| | Reovirus protein s1 |
| | b-Galactosidase M15 truncation mutant |
| | Thyroglobulin |
| | Tubulin |
| | Unassembled immunoglobulin chains |

Hsp90 exists in an equilibrium between an "activated state" prevalent in transformed cells and a "latent state" predominantly in normal cells (Chiosis et al., 2004, Drug Dis. Today, 9: 881-888). The activation state of the chaperone is regulated by co-chaperones and possibly, post-translational modifications. These co-chaperones or co-factors include Hsp70, Hsp70-organizing protein (Hop), p23, cdc37, immunophilins, CHIP PP5, XAP2 Cdc37/p50, Aha, and Hsp40 (Wegele et al., 2004, Rev Physiol Biochem Pharmocol 151: 1-44). Specific co-chaperones may be required for the regulation of specific Hsp90 client proteins.

Active analogs of YSLPGYMVKKLLGA (SEQ ID NO:1) include polypeptides having structural similarity. Structural similarity is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, available at http://www.ncbi.nlm.nih.gov/gorf/b-12.html. Preferably, the default values for all BLAST 2 search parameters are used, including matrix=BLOSUM62; open gap penalty=11, extension gap penalty=1, gap x_dropoff=50, expect=10, word-size=3, and filter on. In the comparison of two amino acid sequences using the BLAST search algorithm, structural similarity is referred to as "identity." Preferably, an active analog of YSLPGYMVKKLLGA (SEQ ID NO:1) has structural similarity of at least 70% identity, more preferably, at least 80% identity, and most preferably, at least 90% identity. Active analogs could be the peptide with the prolyi group in the cis conformation. Active analogs could be the peptide with the prolyl group in the trans conformation. Active analogs could be as small as 12 amino acids or as large as 30 amino acids. Active analogs could include specific modifications that would confer the appropriate stability to the peptide, would confer the ability of the peptide to be properly localized in specific tissue or in a specific compartment of the cell. Thus, the peptide may be modified (e.g., chemically) so that it will be taken up by target cells more readily. For example, it may be constructed in a divalent or multivalent form. Active analogs could include specific post translational modifications such as phosphorylation or the incorporation of specific amino acid analogs that would stabilize the peptide in a pharmaceutically active conformation.

Active analogs can have conservative amino acid substitutions. For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains):Class IV: His, Arg and Lys (representing basic side chains); Class V: Ile, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, gamma-carboxyglutamic acid, beta-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and beta-valine in Class V; and naphthylalanines, substituted phenylalanines, tetrahydroisoquinoline-3-carboxylic acid, and halogenated tyrosines in Class VI.

YSLPGYMVKKLLGA (SEQ ID NO:1), or any combination of its peptide fragments or other active analogs thereof, for example, can be synthetically constructed using known peptide polymerization techniques. For example, the peptides of the invention may be synthesized by the solid phase method using standard methods based on either t-butyloxy-carbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992). Moreover, gene sequence encoding the YSLPGYM-VKKLLGA (SEQ ID NO:1) peptide or analogs thereof can be constructed by known techniques such as expression vectors or plasmids and transfected into suitable microorganisms that will express the DNA sequences thus preparing the peptide for later extraction from the medium in which the microorganism are grown. For example, U.S. Pat. No. 5,595,887 describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

The peptides of the present invention may be employed in a monovalent state (i.e., free peptide or a single peptide fragment coupled to a carrier molecule). The peptides may also be employed as conjugates having more than one (same or different) peptide fragment bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like, are employed as the carrier. Such modifications may increase the apparent affinity and/or change the stability of a peptide. The number of peptide fragments associated with or bound to each carrier can vary, but from about 4 to 8 peptides per carrier molecule are typically obtained under standard coupling conditions.

For instance, peptide/carrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule. For example, conjugates of a peptide coupled to ovalbumin may be prepared by dissolving equal amounts of lyophilized peptide and ovalbumin in a small volume of water. In a second tube, 1-ethyl-3-(3-dimethylamino-propyl)-car-boiimide hydrochloride (EDC; ten times the amount of peptide) is dissolved in a small amount of water. The EDC solution is added to the peptide/ovalbumin mixture and allowed to react for a number of hours. The mixture may then be dialyzed (e.g., into phosphate buffered saline) to obtain a purified solution of peptide/ovalbumin conjugate. Peptide/carrier molecule conjugates prepared by this method typically contain about 4 to 5 peptides per ovalbumin molecule.

The present invention also provides a composition that includes one or more active agents (e.g., YSLPGYM-VKKLLGA (SEQ ID NO:1), at least one active analog thereof) of the invention and one or more carriers, preferably a pharmaceutically acceptable carrier, which could be a pharmaceutically acceptable buffer.

Although not intending to necessarily limit the invention, it is believed that this inhibition occurs upon administration of Hsp90 binding compounds and results in arrest of Rb negative or Rb deficient cells in mitosis. Cyclin D in complex with Cdk4 or Cdk6 and cyclin E-Cdk2 phosphorylate the protein product of the retinoblatoma gene, Rb. Researchers have reported that the protein product of the Rb gene is a nuclear phosphoprotein, which arrests cells during the $G_1$ phase of the cell cycle by repressing transcription of genes involved in the $G_1$ to S phase transition (Weinberg, 1995, Cell, 81:323-330). Dephosphorylated Rb is said to inhibit progression through late $G_1$, in part, through its interaction with E2F transcription family members, which ultimately represses the transcription of E2F target genes (Dyson, 1998, Genes Dev., 12:2245-2262). Progressive phosphorylation of Rb by the cyclin-dependent kinases in mid to late $G_1$ leads to dissociation of Rb from Rb-E2F complexes, allowing the expression of E2F target genes and entry into the S phase.

The retinoblastoma gene product is mutated in several tumor types, such as retinoblastoma, osteosarcoma and small-cell lung cancer. Research also indicates that in many additional human cancers the function of Rb is disrupted through neutralization by a binding protein, (e.g., the human papilloma virus-E7 protein in cervical carcinoma; Ishiji, 2000, J. Dermatol., 27:73-86) or deregulation of pathways uitimateiy responsible for its phoshorylation. Inactivation of the Rb pathway often results from pertubation of p16INKa, Cyclin D1, and Cdk4.

The retinoblastoma gene product, besides being a target of human papilloma E7 protein, is also the target of other oncogenic viral gene products. For example, studies indicate that the simian virus 40 large T antigen inactivates the Rb family of proteins, including Rb, p107, and p130 (Zalvide et al., 1998, Mol. Cell. Biol., 18:1408-1415). Research also indicates that transformation by adenovirus requires E1A binding to Rb (Egan et al., 1989, Oncogene, 4:383-388).

Cells that are Rb negative or Rb deficient uniformly die through apoptotic mechanisms. This mechanism of destroying cells that are Rb negative or Rb deficient provides a means to specifically treat disorders (e.g., cell proliferative disorders and certain viral infections) associated with cells that are Rb negative or Rb deficient.

The destruction of Rb negative or Rb deficient cells can occur with less cytotoxicity to normal cells or tissues. For example, when cells that contain a normal Rb gene product are treated with Hsp90 inhibitors, those cells arrest in $G_1$ of the cell cycle and, in some cases, may differentiate and die. However, cells that are Rb negative or Rb deficient uniformly die when treated with Hsp90 inhibitors. Further, such cells will be more susceptible to other agents or radiation treatments and will require lower doses of drug for killing than cells with wild-type retinoblastoma gene product. Studies indicate that the $G_2$/M phase of the cell cycle is the most radiosensitive phase of the cell cycle (Sinclair, 1968, Radiat. Res., 33:620).

In one embodiment of the invention, the $IC_{50}$ of the Hsp90 inhibitor used in the methods to destroy cells that are Rb negative of Rb deficient is lower than the $IC_{50}$ against similar cells that are not Rb negative or deficient. Preferably, the $IC_{50}$ is at least 5-fold lower, more preferably at least 10-fold lower, still further at least 20-fold lower, and most preferably at least 30- to 50-fold lower, when compared to similar cells that are not Rb negative or deficient (e.g., wild-type Rb-containing cells). As used herein, "$IC_{50}$" is defined as the concentration of an Hsp90 inhibitor required to achieve killing of 50% of cells.

Preferably, a disorder that has associated cells that are Rb negative or Rb deficient is a cell proliferative disorder (e.g., tumorigenesis) or a viral infection, for example. Thus, the present invention provides a method for treating (e.g., prophylactically or therapeutically) a cell proliferative disorder, a method for treating (e.g., prophylactically or therapeutically) tumorigenesis, a method for treating (e.g., prophylactically or therapeutically) a viral infection in a subject, a method for treating a subject for a disorder in which Hsp90 plays a role in the progression of the disorder (for example, by regulating a client protein where increased or decreased amounts of, or increased or decreased activity of, the client protein is responsible for the disorder).

The methods of this invention are useful for treating cell proliferative disorders (e.g., diseases) associated with Rb negative or Rb deficient. Cell proliferative disorders refer to disorders wherein unwanted cell proliferation of one or more subset(s) of cells in a multicellular organism occurs, resulting in harm, for example, pain or decreased life expectancy to the organism.

Cell proliferative disorders include, but are not limited to, tumors, benign tumors, blood vessel proliferative disorders, autoimmune disorders, and fibrotic disorders. Specific examples include retinoblastoma, osteosarcoma, breast cancers, bladder cancer, prostate cancer, renal carcinoma, cancers associated with viral infections, such as cervical cancers associated with human papilloma virus, and small-cell lung cancer. Additionally, the methods of the invention are useful for the treatment of certain viral infections which result in an Rb negative phenotype, such as human papilloma virus.

The preferred effect of the methods of the instant invention, with respect to cell proliferative disorders, is the inhibition, to some extent, of growth of cells causing or contributing to a cell proliferative disorder. A therapeutic effect relieves to some extent one or more of the symptoms of a cell proliferative disorder. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; and/or 5) relieving to some extent one or more of the symptoms associated with the disorder.

In reference to the treatment of a cell proliferative disorder other than a cancer, a desired effect refers to either: 1) the inhibition, to some extent, of the growth of cells causing the disorder; 2) the inhibition, to some extent, of the production of factors (e.g., growth factors) causing the disorder; and/or 3) relieving to some extent one or more of the symptoms associated with the disorder.

With respect to viral infections, the preferred desired effect is the inhibition of a viral infection. More preferably, the desired effect is the destruction of cells which contain the virus.

The methods of the present invention may be used on mammals, preferably humans, either alone or in combination with other therapies or methods useful for treating a particular cell proliferative disorder or viral infection.

The use of the present invention is preferably facilitated by first identifying whether the cell proliferation disorder (i.e., cell proliferative disorder) or viral infection is accompanied by cells which contain altered expression of the Rb gene product. Once such disorders are identified, subjects suffering from such a disorder can be identified by analysis of their symptoms by procedures well known to medical doctors. Such subjects can then be treated as described herein.

The determination of whether the cell proliferation disorder is associated with an altered expression of the Rb gene product can be carried out by first determining the protein expression of Rb in the appropriate cells isolated from a mammal suspected of having a cell proliferative disorder or viral infection. For example, in the case of small-cell lung cancer, the protein expression of Rb determined from cells isolated from a mammal suspected of having small cell lung cancer can be compared to the appropriate cells isolated from a disease free mammal.

Rb expression and/or mutations can be measured using methods well known in the art, including, but not limited to, immunohistochemistry, Southern blot analysis, and Northern blot analysis. The use of immunohistochemistry (e.g., Western blot analysis) to determine Rb expression is described by Higashiyama et al., 1994, Oncology, 51:544-551, and Kohn, 1997, J. Gastroenterol. Hepatol., 12:198-203. The use of Southern blot analysis to determine defects in the Rb gene is demonstrated by Presti et al., 1996, Anticancer Res., 16:549-556. The determination of Rb mRNA using Northern blot analysis is demonstrated by Rygaard et al., 1990, Cancer Res., 50:5312-5317. If the analysis indicates that there is altered Rb expression, the subject is a candidate for treatment using the methods described herein.

In the case of cell proliferative disorders arising due to unwanted proliferation of non-cancer cells, the level of the Rb gene product is compared to that level occurring in the general population (e.g., the average level occurring in the general population of people or animals excluding those people or animals suffering from a cell proliferative disorder). If the unwanted cell proliferation disorder is characterized by an abnormal level of Rb than occurring in the general population, then the disorder is a candidate for treatment using the methods described herein.

Scientists estimate that over 70 types of papilloma viruses infect humans (HPV) (Sasagawa et al., 1996, Clinical Diag. Lab. Immunol, 3:403-410). Of these several are associated with malignancies of humans, particularly cervical cancers (Bosch, 1995, J. Natl. Cancer Inst., 87:796-802). Recent evidence also implicates HPV in some head and neck cancers. Several types of HPV are associated with an intermediate to high risk of malignancies (types 16, 18, 31, 33, 35, 45, and 56) (Sasagawa et al., 1996, Clinical Diag. Lab. Immunol., 3:403-410). In infections with these HPV, the viral genome integrates into the genome of the infected cell with subsequent expression of transforming genes E6 and E7. Data indicate that the products of these genes may promote malignant transformation by altering the functions of two cellular tumor suppressor proteins (p53 and Rb). E6 causes the proteolytic degradation of p53 (Scheffiner et al., 1990, Cell, 63:1129-1136. E7 complexes with Rb causing its release from transcription factor E2F, leading to the activation of genes involved in cell proliferation (Dyson et al., February 1989, Science, 243:934-937). Methods to determine HPV association with cervical cancer are known (e.g., Sasagawa et al., 1996, Clinical Diag. Lab. Immunol., 3:403-410).

Cell proliferative disorders, including those referenced above, are not necessarily independent. For example, fibrotic disorders may be related to, or overlap with, blood vessel disorders. Additionally, for example, atherosclerosis (which is characterized herein as a blood vessel disorder) is associated with the abnormal formation of fibrous tissue.

A cancer cell refers to various types of malignant neoplasms, most of which can invade surrounding tissues, and may metastasize to different sites.

The formation and spreading of blood vessels, or vasculogenesis and angiogenesis respectively, play important roles in a variety of physiological processes such as embryonic development, wound healing and organ regeneration. They also play a role in cancer development. Blood vessel proliferation disorders refer to angiogenic and vasculogenic disorders generally resulting in abnormal proliferation of blood vessels. Examples of such disorders include restenosis, retinopathies, and atherosclerosis.

As noted above, other such proliferative disorders can be identified by standard techniques, and by determination of the efficacy of action of the compounds described herein.

The methods of the invention typically include administering to (e.g., applying to the skin of) a subject (preferably a mammal, and more preferably a human) a composition of the invention in an amount effective to produce the desired effect. The term "effective amount" as used herein, means an amount of a peptide utilized in the methods of the present invention which is capable of providing a desired effect. The specific dose of compound administered according to this invention to obtain therapeutic and/or prophylactic effects will, of course, be determined by the particular circumstances surrounding the case, including, for example, the compound administered, the route of administration, the condition being treated and the individual being treated.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949. A typical daily dose (administered in single or divided doses) will contain a dosage level of from about 0.01 mg/kg to about 50 mg/kg of body weight of a peptide of this invention. Preferred daily doses generally will be from about 0.05 mg/kg to about 20 mg/kg and ideally from about 0.1 mg/kg to about 10 mg/kg.

The active agents of the present invention can be formulated for enteral administration (oral, rectal, etc.) or parenteral administration (injection, internal pump, etc.). The administration can be via direct injection into tissue, interarterial injection, intervenous injection, or other internal administration procedures, such as through the use of an implanted pump, or via contacting the composition with a mucus membrane in a carrier designed to facilitate transmission of the composition across the mucus membrane such as a suppository, eye drops, inhaler, or other similar administration method or via oral administration in the form of a syrup, a liquid, a pill, capsule, gel coated tablet, or other similar oral administration method. The active agents can be incorporated into an adhesive plaster, a patch, a gum, and the like, or it can be encapsulated or incorporated into a bio-erodible matrix for controlled release.

The carriers for internal administration can be any carriers commonly used to facilitate the internal administration of compositions such as plasma, sterile saline solution, IV solutions, or the like. Carriers for administration through mucus membranes can be any well-known in the art. Carriers for administration oral can be any carrier well-known in the art.

The formulations may be conveniently presented in unit dosage form and may be prepared by any of the methods well known in the art of pharmacy. All methods include the step of bringing the active agent into association with a carrier which constitutes one or more accessory ingredients. In general, the formulations are prepared by uniformly and intimately bringing the active agent into association with a liquid carrier, a finely divided solid carrier, or both, and then, if necessary, shaping the product into the desired formulations.

Formulations suitable for parenteral administration conveniently include a sterile aqueous preparation of the active agent, or dispersions of sterile powders of the active agent, which are preferably isotonic with the blood of the recipient. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. The amount of active agent is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, DMSO, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

In a particularly preferred embodiment, the active agents of the present invention can be used in cosmetic formulations (e.g., skincare cream, sunscreen, decorative make-up products, and other dermatological compositions) in various pharmaceutical dosage forms, and especially in the form of oil-in-water or water-in-oil emulsions, solutions, gels, or vesicular dispersions. The cosmetic formulations may take the form of a cream that can be applied either to the face or to the scalp and hair, as well as to the human body. They can also serve as a base for a lipstick.

Particularly preferred cosmetic formulations can also include additives such as are usually used in such formulations, for example preservatives, bactericides, perfumes, antifoams, dyes, pigments which have a coloring action, surfactants, thickeners, suspending agents, fillers, moisturizers and/or humectants, fats, oils, waxes or other customary constituents of a cosmetic formulation, such as alcohols, polyols, polymers, foam stabilizers, electrolytes, organic solvents, or silicone derivatives.

Cosmetic formulations typically include a lipid phase and often an aqueous phase. The lipid phase can advantageously be chosen from the following group of substances:mineral oils, mineral waxes oils, such as triglycerides of capric or of caprylic acid, but preferably castor oil; fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids; alkyl benzoates; silicone oils, such as dimethylpolysiloxanes, diethylpolysiloxanes, diphenylpolysiloxanes and mixed forms thereof.

If appropriate, the aqueous phase of the formulations according to the invention advantageously includes alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum, and hydroxypropylmethylcellulose, particularly advantageously from the group consisting of poly-acrylates, preferably a polyacrylate from the group consisting of so-called CARBOPOLS, for example CARBOPOLS of types 980, 981, 1382, 2984, and 5984, in each case individually or in combination.

EXAMPLES

Objects and advantages of this invention are further illustrated by the following examples, but the particular materials and amounts thereof recited in these examples, as well as other conditions and details, should not be construed to unduly limit this invention.

Peptides.

Synthetic peptides were obtained from the Protein Core Research Facility at the University of Nebraska-Lincoln and the Biotechnology Center at Utah State University-Logan. Dilysine was obtained from Sigma Chemical, Co.

Antibodies.

Antibody to beta-COP was obtained from Oncogene Research Products (EMD Biosciences, Ind.) (Product No. PC175) and used at a 1:1500 dilution. Antibody to mouse Hsp90α was obtained from Stressgen (Victoria, Canada), Product No. SPS-771 and used at a 1:1000 dilution.

Synthesis of Sulfolink-peptide Affinity Matrix.

Sulfolink-peptide affinity columns were synthesized using the Sulpholink Kit (Pierce Biotechnology, Inc., Rockford, Ill., Product No. 44895) according to their protocol. Peptides were stored at 4° C. in a lyophilized state in a sealed desiccator. Approximately 2 mg of peptide is weighed and suspended in 0.4 ml of DMSO. This peptide solution is immediately diluted into 2 ml of coupling buffer and mixed (100 µl is removed for quantization) then added to 4 ml of a 50% slurry of Sulfolink gel equilibrated in coupling buffer in a small plastic column. The combination is mixed for 15 minutes at room temperature by rotation. The mixture is further incubated for 30 minutes at room temperature without mixing. The column is washed with coupling buffer, then blocked with freshly made 0.5 M cysteine, further washed with a Wash buffer. The peptide affinity matrix was removed from the column to a 50 ml conical tube and stored as a 50% slurry in PBS containing 0.05% sodium azide at 4° C.

Preparation of Mouse Brain Extract.

Total mouse brain from deeply anthesized adult mice is excised and flash frozen in liquid nitrogen and stored at −80° C. The frozen brain is pulverized in a mortar and pestle under liquid nitrogen and suspended in TNGD (TRIS 50 mM pH7.5, NaCl 75 mM, EGTA 10 mM, EDTA 2 mM) with protease inhibitors (10 µl/ml of protease inhibitor cocktail for mammalian cells, Sigma Chemical Co. No. P8340) at 1 ml/100 mg of tissue. This mixture is homogenized in a Potter-Elvehjem Teflon glass homogenizer on ice. The homogenate is centrifuged for 10 minutes at 4° C. in an IEC minifuge at 13,200 RPM. The pellet is discarded. The supernatant is used immediately or frozen and stored at −80° C.

Binding Assay: Protein Purification on Peptide Affinity Matrix.

All steps of protein purification were done at 4° C. in a Handee Spin Cup Column (Pierce Biotechnology, Inc., Rockford, Ill., Product No. 69700) in the presence of protease inibitor (10 µl/ml of protease inhibitor cocktail for mammalian cells, Sigma Chemical Co. No. P8340). Fifty µl of a 50% slurry of Sulfolink-peptide was washed five times with 0.4 ml of TNGD. Mouse brain extract supernatant (100 µl) was allowed to absorb to the gel by mixing by rotation for 30 minutes. Following absorption the gel is washed five times with 0.4 ml TNGD. Specific elution is described in the results.

SDS Gel Electrophoresis and Western Analysis.

Protein samples are made 1× with ImmunoPure Lane Marker Non-Reducing Sample Buffer (5×) (Pierce Biotechnology) and heated for 5 minutes at 95° C. Samples are separated on a 4-20% Linear Gradient Ready Gel (BIO-RAD Laboratories, Hercules, Calif., Product No. 161-1105). Polyacrylamide gels are stained with BIORAD Silver Stain Plus Kit (No. 161-0449) or Bio-Safe Coomassie Stain or electroblotted to PVDF membrane (BIO-RAD) for Western blot analysis, according to directions provided by the manufacturer. Specific antibody binding is detected using ECL Western Blotting System (Amersham Biosciences Corp., Piscataway, N.J., Product No. RPN2108). Molecular weight standards used were the BIO-RAD Precision Protein Standards, Prestained, Broad Range (Product No. 161-0372). Chemiluminecence is detected using Kodak Biomax ML Scientific Imaging Film (Product No. 868-9358).

Mass Spectrometry of Eluted Protein P97.

Mass spectrometry (MS) was done at the Nebraska Center for Mass Spectrometry at the University of Nebraska, Lincoln. Samples for MS were separated on a 4-20% linear gradient Ready Gel, stained with BIO-Safe Coomassie stain, rinsed in water and cut out of the gel and shipped to the facility in 20% methanol and 5% acetic acid.

OTOF C-terminus Affinity Binding

Four Sulpholink peptide affinity matrix were constructed. Each of the peptides included an added N-terminal cysteine that enables coupling to the Sulfolink matrix. Peptide OTOF CTERM E47 corresponds to the C-terminus 14 amino acids of the otoferlin isoform found in brain (which includes exon 47 and exon 48) (see Table 2) (Yasunaga, 2000, Am. J. Hum.

Genet., 67:591-600). OTOF CTERM E48 corresponds to the C-terminus 14 amino acids of the otoferlin isoform found in cochlea (which excludes exon 47 but includes exon 48). Peptide 670 CC1 and 672 BC1 correspond to the E48 and E47 peptide respectively with the di-lysine replaced with di-serine.

TABLE 2

Peptide composition of Sulfolink peptide affinity columns

| Peptide name | Peptide sequence | Added peptide | Coupling efficiency |
| --- | --- | --- | --- |
| OTOF CTERM E47 | CYSLPGYLAKKILGA (SEQ ID NO:3) | 1.8 mg | 65% |
| OTOF CTERM E48 | CYSLPGYMVKKLLGA (SEQ ID NO:2) | 2.3 | 46 |
| 670 CC1 | CYSLPGYMVSSLLGA (SEQ ID NO:4) | 2.1 | 78 |
| 672 BC1 | CYSLPGYLASSILGA (SEQ ID NO:5) | 2.3 | 75 |

Mouse brain extracts were absorbed to the four peptide matrix columns as described in the methods. Column matrix was transferred to PCR tubes and made 1× with SDS buffer and heated for 5 minutes at 95° C. After heating the samples were centrifuged for 1 minute at 300×g and the supernatant separated by SDS gel electrophoresis on two separate gels.

Figure 1B:
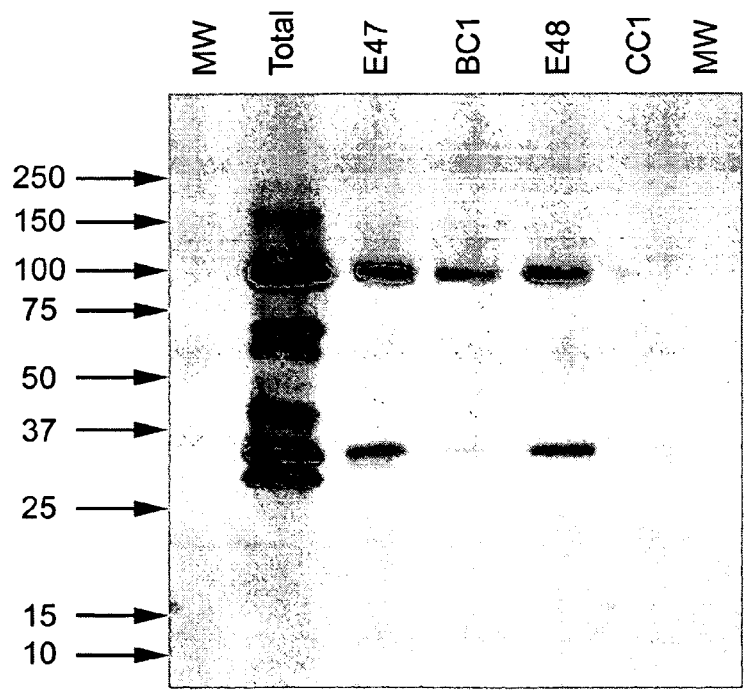

FIG. 1A shows the gel stained with commassie blue. The protein eluted from the four gel matrix are quite similar except for the OTOF CTERM E48 matrix which shows higher levels of a protein at approximately 97 kilo-daltons. FIG. 1B shows the result of western analysis of an identical gel using antibody against beta-COP. This antibody recognizes the appropriate size protein in the total extract and in the elution from each of the column matrix. The amount of beta-COP binding OTOF CTERM E47 and OTOF CTERM E48 is similar. The E47 peptide control 672 BC1 bound about half the amount of OTOF CTERM E47. The E48 peptide control 670 CC1 bound about a tenth of the OTOF CTERM E48 peptide matrix. Smaller molecular weight bands are apparently due to proteolysis of beta-COP.

Figure 2:
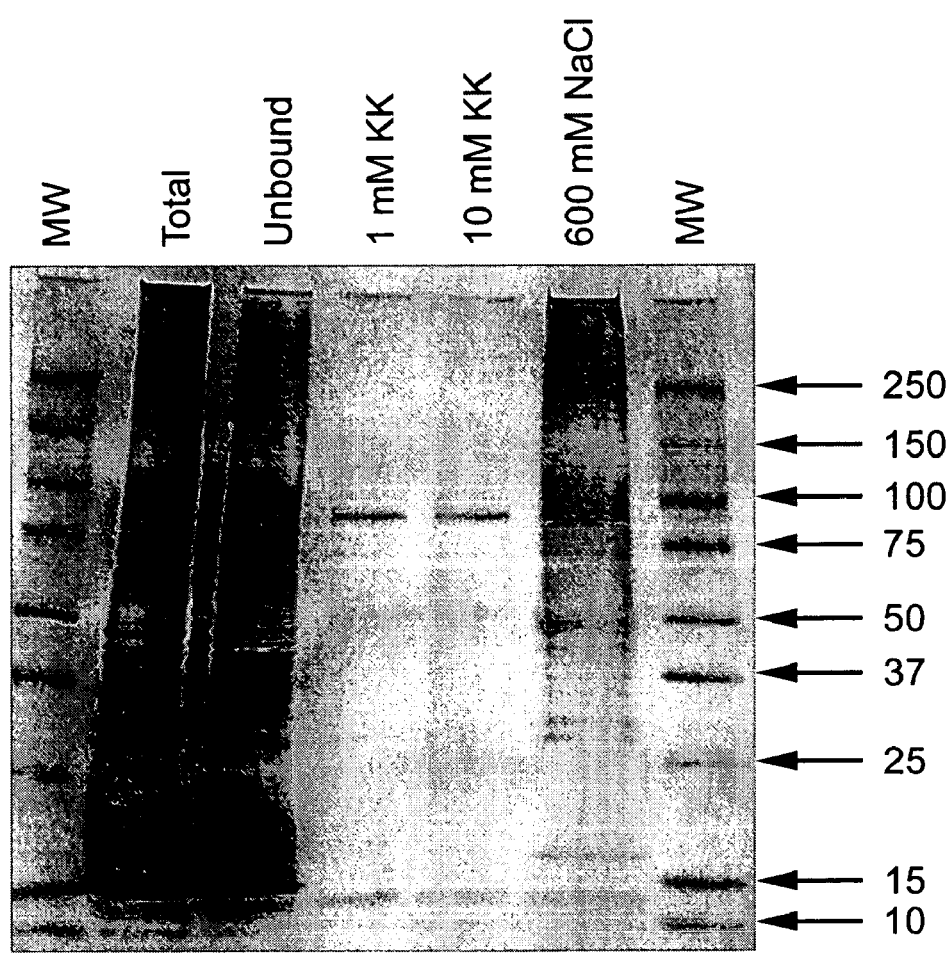
FIG. 2. Elution of OTOF CTERM E48 (CYSLPGYM-VKKLLGA (SEQ ID NO:2)) with di-lysine and high salt. MW=molecular weight markers. Total=mouse brain 13,200 rpm supernatant loaded onto column matrix. Unbound=mouse brain supernatant that did not bind the column. 1 mM KK=protein eluted with 1 mM dilysine in TNGD. 10 mM KK=10 mM dilysine in TNGD. Six hundred (600) mM NaCl=protein eluted with 600 mM NaCl in TNGD.

The working hypothesis was that the major protein band that should bind the otoferlin C-terminus affinity columns should be gamma-COP a subunit of the coatomer complex. It was suspected that the specific band seen in elution of the OTOF CTERM E48 was gamma-COP. Since there was no commercially available antibody to this protein, further purification of the OTOF CTERM E48 binding protein was carried out. Initially block NaCl elution using 0.3 M NaCl, 0.6 M NaCl and 1.0 M NaCl was attempted. The 0.3 M NaCl elution was successful but not specific (data not shown). As expected and supported by data shown in FIG. 2, the key amino acids in the binding peptide are the two lysine residues. The column was eluted with both 1 mM and 10 mM dilsyine. FIG. 2 shows that both concentrations of dilysine and 600 mM NaCl successfully elute a protein initially designated as p97. Dilysine elutes this protein and a smaller protein of about 14,000 daltons specifically.

Identification of E48 C-terminus Binding Protein

The p97 protein was cut from the dilysine eluted lanes (FIG. 2) and submitted for mass spectrometry analysis. The protein with the highest identity score of peptide composition to the submitted sample is HS9A_MOUSE, heat shock protein HSP-90 alpha (HSP 86).

Identification of e48 C-terminus Binding Protein

Figure 3:
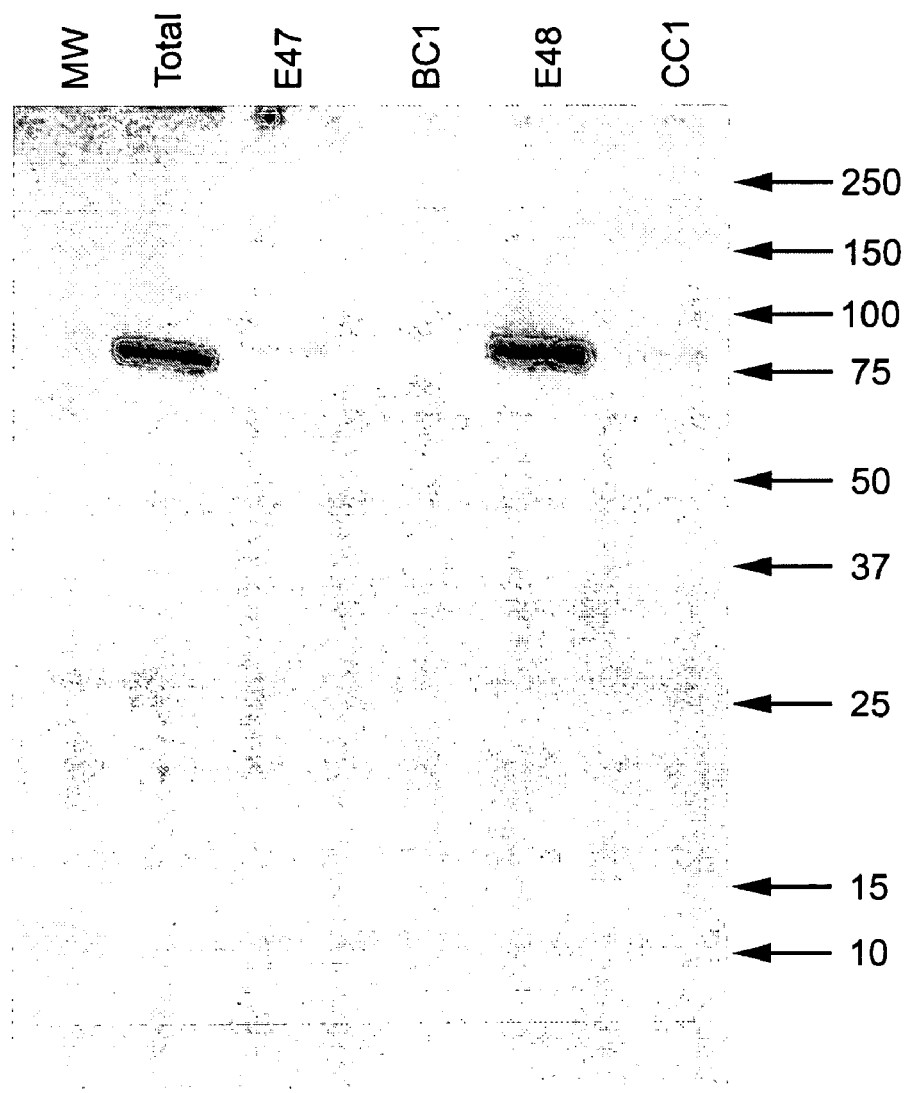
FIG. 3. Western analysis of protein bound to peptide affinity columns. The identical samples shown in FIG. 1 were separated on a 4-20% SDS-PAGE, transferred to PVDF membrane and probed with antibody to Hsp90α detected by chemiluminescence. MW=molecular weight markers, Total=13,200 rpm supernatant loaded onto column matrix. E47=sample eluted from OTOF CTERM E47 column matrix. E48=eluted from OTOF CTERM E48 column matrix. Sample BC1 and CC1 peptides are specific controls for E47 and E48 respectively where a di-serine replaces di-lysine.
Figure 4:
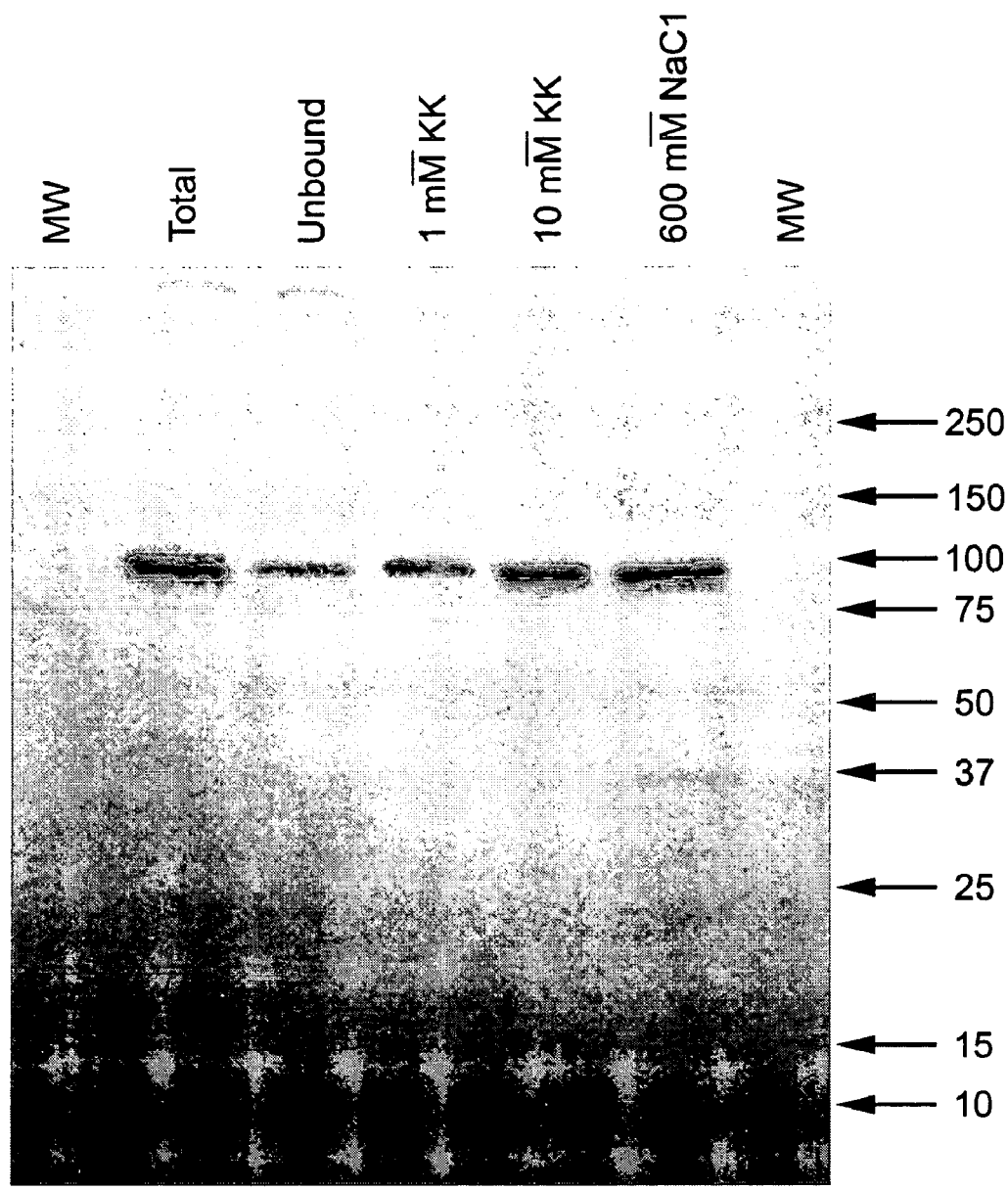
FIG. 4. Western analysis of protein bound to OTOF CTERM E48 peptide affinity column and eluted with di-lysine and high salt. The identical samples shown in FIG. 2 were separated on a 4-20% SDS-PAGE, transferred to PVDF membrane and probed with antibody to Hsp90α detected by chemiluminescence. MW=molecular weight markers. Total=mouse brain 13,200 rpm supernatant loaded onto column matrix. Unbound=mouse brain supernatant that did not bind the column. One (1) mM KK=protein eluted with 1 mM di-lysine in TNGD. Ten (10) mM KK=10 mM di-lysine in TNGD. Six hundred (600) mM NaCl=protein eluted with 600 mM NaCl in TNGD.

Identical SDS-PAGE gels with the same samples in the same order as FIG. 1 and FIG. 2 were run and processed for western analysis. FIGS. 3 and 4 confirm by western analysis that the p97 peptide eluted with di-lysine and identified by mass spectroscopy is Hsp90α.

Fifty μl of 50% slurry of OTOF CTERM E47 and OTOF CTERM E48 Sulfolink affinity matrix were equilibrated with four washes of 0.4 ml of TNGD buffer in Handee Spin Cup Columns (Pierce, Rockford). The columns was preabsorbed with 100 μl of 10% BSA for 30 minutes at 4° C. and mixed by rotation. The columns were then washed five times with 0.4 ml of TNGD. Four hundred (400) ng of recombinant human Hsp90α (Stressgen SPP-776, Lot No. B201401) in 100 μl of TNGD was added to each column for 30 minutes at 4° C. and mixed by rotation. The unabsorbed protein was removed by centrifugation. The columns were washed five times with 0.4 ml of TNGD, then eluted with 100 μl TNGD+600 mM NaCl. Samples were analyzed on a 4-20% SDS-PAGE gel followed by silver staining using a BIORAD Silver Stain Plus kit (No. 161-0449) as show in FIG. 5. This figure shows that Hsp90α specifically binds the OTOF CTERM E48, but does not bind OTOF CTERM E47 under these conditions; however, it is believed that OTOF CTERM E47 would bind to this protein (or another of the Hsp90 class of proteins) under other conditions. The amount of protein added and eluted was determined by scanning the silver stained gel using a Alpha Imager 2200 gel imaging system. Approximately 10% of the protein corresponding to Hsp90 molecular weight was eluted with 600 mM NaCl+TGND from the E48 column while no eluted protein was detected with the same elution conditions from the E47 column.

The discovery of the binding of Hsp90 to the peptide matrix corresponding to YSLPGYMVKKLLGA (SEQ ID NO:1) lead to a closer examination of that peptide sequence. Inspection of the peptide sequence revealed the existence of a potential prolyl-peptidyl cis-trans isomerase motif in the OTOF CTERM E48 and OTOF CTERM E47 peptide, with adjacent tyrosine and serine residues that may allow phosphorylation control of a sterically-switchable di-lysine motif. A search of the literature lead to the finding of similarity in sequence of YSLPGYMVKKLLGA (SEQ ID NO:1) to an optimal peptide substrate of the peptidyl-prolyl cis-trans isomerase, Pin 1 (Zhou et al., 1999, Cell Mol Life Sci, 56:788-806). The prolyl isomerase Pin1 has been implicated in regulating cell cycle progression (Winkler et al., 2000, Science 287:1644-1647; Ryo et al., 2003, J Cell Sci 116:773-783). It is believed that Pintide (the sequence of which is disclosed in Zhou et al., 1999, Cell Mol Life Sci, 56:788-806), which inhibits the peptidyl prolyl isomerase, Pin1, does not bind to an Hsp90 protein, and therefore it is believed that this peptide would not inhibit the ability of an Hsp90 protein to regulate client proteins (hence, not within the scope of an active analog of YSLPGYMVKKLLGA (SEQ ID NO:1)).

Searching the literature for other peptides with biological activity that have sequence similarity to YSLPGYMVKKLLGA (SEQ ID NO:1) identified two peptides derived from wasp venom, mastoparan and mastoparan X. Mastoparans are peptides from wasp venom that show many biological activities (Kuhn-Nentwig, 2003, Cell. Mol. Life Sci., 60:2651-2668). It is believed that the mastoparan and mastoparan X peptides (the sequences of which is disclosed in Kuhn-Nentwig, 2003, Cell. Mol. Life Sci., 60:2651-2668) do not bind to an Hsp90 protein, and therefore it is believed that these peptides would not inhibit the ability of an Hsp90 protein to regulate client proteins (hence, not within the scope of an active analog of YSLPGYMVKKLLGA (SEQ ID NO:1)).

Discussion.

Figure 6:
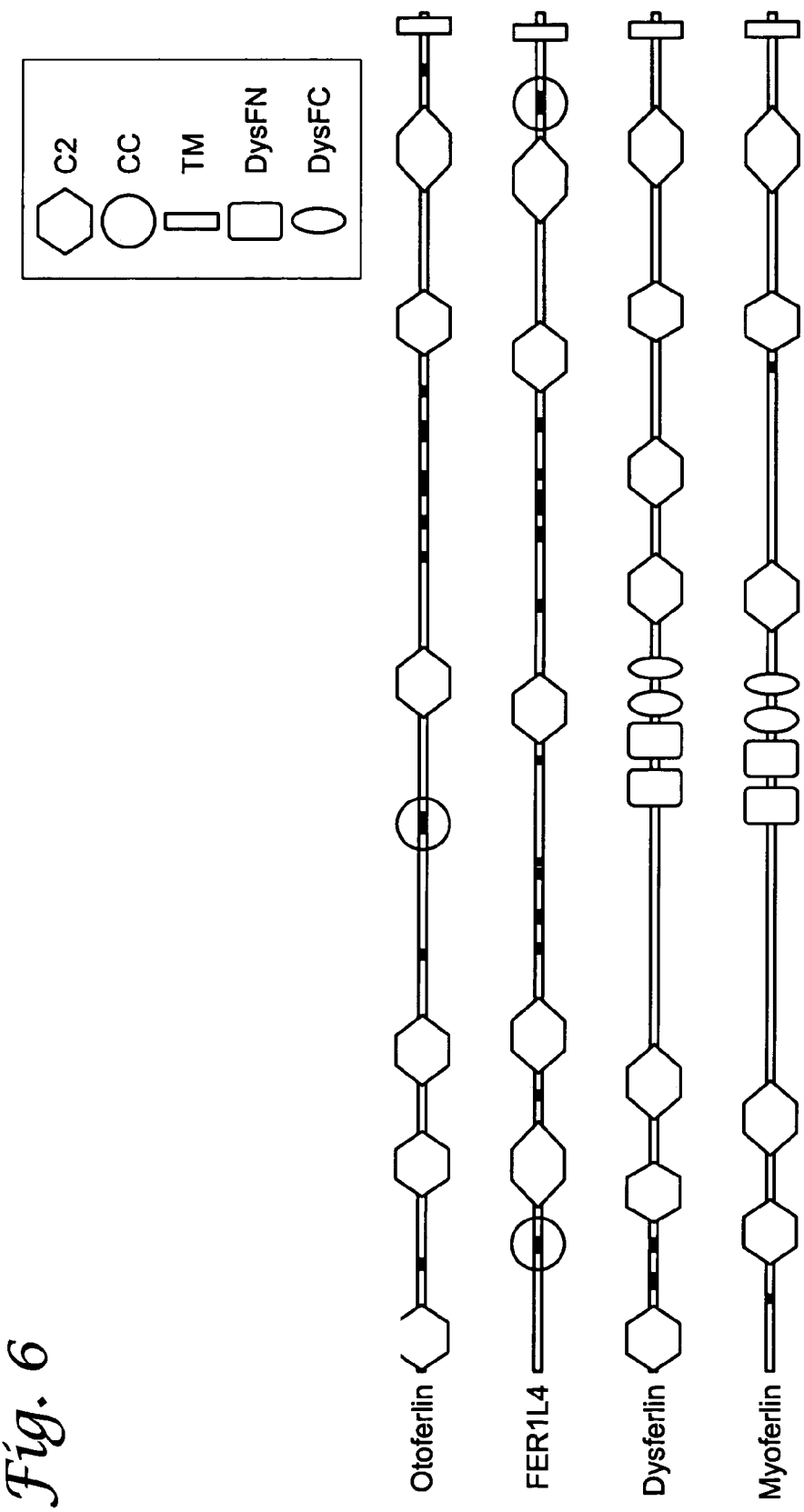
FIG. 6. Protein motif organization for human ferlin gene family. As determined by SMART (Schultz et al., 1998, Proc. Natl. Acad. Sci. USA, 95:5857-5864; Letunic et al., 2002, Nucleic Acids Res., 30:242-244). C2 is the calcium binding motif, CC is a coiled coil domain, TM is the transmembrane domain DysFN is the dysferin domain amino-terminal and DysFC is the dysferlin domain carboxy terminal region.

This Hsp90 binding peptide was discovered during the study of an unusual type of hearing loss called auditory neuropathy/dyssynchrony. Auditory neuropathy/dyssynchrony is a type of hearing loss where one can sometimes hear puretone sound but not be able to understand speech. The timing of neural transmission in the auditory system is disturbed. Mutations in the gene encoding otoferlin can cause an auditory neuropathy/dyssynchrony type hearing loss (Yasunaga et al., 1999, Nat. Genet., 21:363-369; Varga et al., 2003, J. Med. Genet., 40:45-50). Several alternatively spliced forms of otoferlin mRNA exist (Yasunaga et al., 2000, Am. J. Hum. Genet., 67:591-600). In humans, both a 5 kb and a 7 kb form were found, as well as specific spliced forms found only in the cochlea and others found in both the brain and the cochlea. In the mouse, only long isoforms have been detected. Mouse brain and mouse cochlea have distinct isoforms. Except for the absence of a mouse short isoform, tissue specific isoform expression is concordant in mouse and human (Yasunaga et al., 2000, Am. J. Hum. Genet., 67:591-600). The gene has 48 exons; exon 47 is skipped in cochlea, heart, kidney and total fetus, leading to a different C-terminal peptide sequence. Otoferlin is a member of a small family of genes including dysferlin, myoferlin and FER1L4 (FIG. 6).

Recent experimental results have identified a functional role for a closely related protein, dysferlin. Mutations in dysferlin cause several types of muscular dystrophy (Bushby, 2002, Acta Neurol. Belg., 100: 142-5). This experimental evidence indicates that dysferlin is a calcium-activated membrane-fusion trigger protein involved in the repair of muscle sarcolemma (Bansal et al., 2003, Nature, 423:168-72; Bansal et al., 2004, Trends Cell. Biol., 14:206-213).

A calcium activated mechanism for membrane resealing has been known for some time (Mayorga et al., 1994, J. Biol. Chem., 269:30927-30934; Steinhardt et al., 1994, Science, 263:390-393; Bi et al., 1995, J. Cell. Biol., 131:1747-1758; Miyake et al., 1995, J. Cell. Biol., 131:1737-1745; McNeil et al., 2001, Nat. Cell Biol., 3:E124-E129). The membrane repair system is activated by an influx of calcium through a wound. The local influx of calcium at the site of the injury triggers the fusion of vesicles with one another and then with the plasma membrane creating a "patch" across the wound area. Dysferlin acts as a calcium-activated membrane-fusion trigger protein. A mounting body of evidence shows cell membrane resealing is accomplished by a vesicular mechanism similar to neurotransmitter release (Steinhardt et al., 1994, Science, 263:390-393; Detrait et al., 2000, J. Neurobiol., 44:382-391).

It is well established that the carboxy-terminal dilysine motif is an endoplasmic reticulum trafficking signal (Goldberg, 2000, Cell, 100:671-9; Andersson, 1999, J. Biol. Chem., 274:15080-4; Letourneur et al., 1994, Cell 79:1199-207). Proteins with such signals are targeted for the COPI trafficking pathway. COPI coat proteins include coatomer and ADP-ribosylation factor 1(ARF1). Coatomer is a protein complex composed of seven subunits; alpha, beta, beta', gamma, delta, epsilon, and zeta COP which form a coat around targeted membrane forming a coated vesicle.

The underlying hypothesis is that otoferlin has two functional domains that are separated topologically. The cytoplasmic domain consists of six C2 domains and a coiled-coil domain. Elevated calcium concentration detected by increased binding of calcium to the otoferlin C2 domains triggers a membrane fusion process which allows "patching" of plasma membrane damage. The second functional domain of otoferlin is the C-terminal luminal domain, a switching-targeting domain that recycles the membrane "patch" using a COPI vesicle trafficking pathway.

Figure 5:
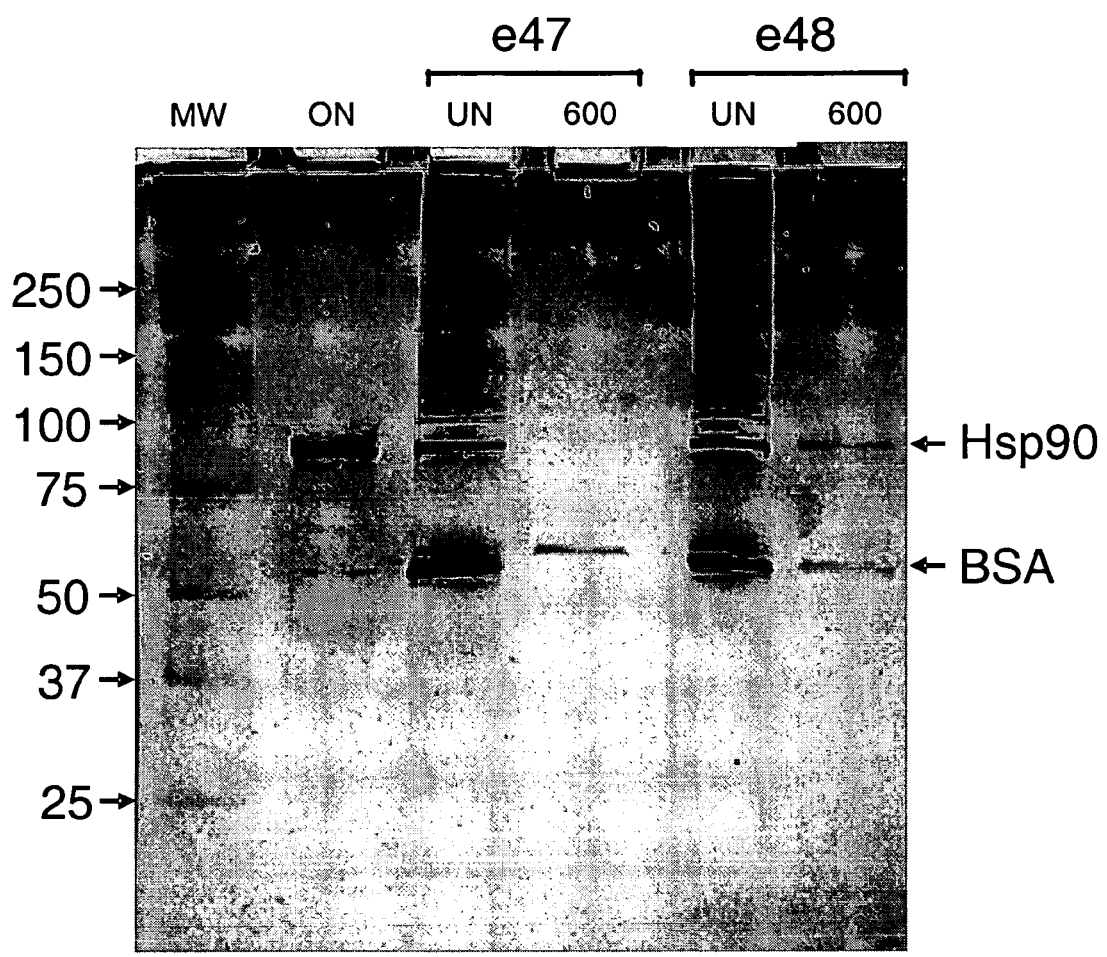
FIG. 5. Silver stained Hsp90α protein bound to peptide affinity columns. Lane ON show Hsp90α loaded on an E47 and E48 peptide affinity column. Lane UN shows the protein that did not bind to the affinity column for the E47 and E48 peptide affinity column respectively. Lane 600 show the protein eluted from the column with 600 mM NaCl in TNGD. Peptide columns were pre-absorbed with 10% bovine serum albumin (BSA) for 30 min at 4° C. prior to absorption with purified Hsp90α.

The coatomer protein I (COPI) complex is predicted to bind to the di-lysine motif via its gamma subunit. COPI coat proteins include coatomer and ADP-ribosylation factor 1 (ARF1). Coatomer is a protein complex composed of seven subunits; alpha, beta, beta', gamma, delta, epsilon and zeta COP which form a coat around targeted membrane, forming a coated vesicle. There is no antibody to the gamma coatomer subunit that is commercially available but antibodies are available for both the beta subunit and the alpha subunit. Isoform-specific peptide affinity matrices were constructed to differentiate specific binding to the isoform found in the cochlea from that found in the brain. Protein binding to these affinity matrices was analyzed by SDS polyacrylamide gel electrophoresis (PAGE) and western blot analysis. Coomassie blue staining of the SDS PAGE showed specific binding of a 97-kilodalton protein to the exon 48 (E48) otoferlin C-terminal peptide matrix but not the exon 47 (E47) otoferlin C-terminal peptide matrix (FIG. 1A). Western blot analysis showed the specific binding of the beta subunit of coatomer to both the E47 and E48 otoferlin affinity matrices, indicating coatomer complex binding (FIG. 1B). Our original assumption was that the stained protein (97-kilodalton protein) was a specific coatomer subunit. This protein could be eluted from the peptide affinity column with 1 mM di-lysine (FIG. 2). Mass spectroscopy identified this protein as HS9A_MOUSE, heat shock protein Hsp90α (HSP 86). This identification has been confirmed by western blot analysis (see FIG. 3 and FIG. 4) as well as specific binding of purified human Hsp90α to the E48 otoferlin C-terminal peptide (FIG. 5).

The discovery of a specific association with Hsp90 with the otoferlin cochlear di-lysine motif was unexpected and prompted re-examination of the 14 amino acid motif. Adjacent to the di-lysine motif is a Ser-Leu-Pro motif that is a presumptive peptidyl-prolyl cis-trans isomerase substrate that would potentially make this di-lysine targeting motif, a sterically-switchable targeting motif. Hsp90 functions as a chaperone that specializes in controlling the activity, turnover, and trafficking of proteins involved in signal transduction (Young et al., 2001, J. Cell. Biol., 154:267-273; Pratt et al., 2003, Exp. Biol. Med., 228:111-133). Chaperones are a class of proteins that catalyze protein folding, assembly, repair and degradation (Young et al., 2003, Trends Biochem. Sci., 28:541-547).

Hsp90 is best known for its role in mediating activation of transcription by steroid hormones. It plays an important role in the activation of several "client" proteins including several hormone receptors, signaling kinases, and G-proteins. Hsp90 plays an important role in cellular response to hypoxia (Su et al., 2000, Am. J. Physiol. Lung Cell Mol. Physiol., 278: L1204-L1212; Chen et al., 2004, Lab. Invest., 84:182-190). Hsp90 is involved in the activation of a heme-regulated transcription factor and a heme-regulated kinase important in protein translation (Shao et al., 2002, Biochemistry, 41:6770-6779). It is also required in the replication of specific viruses (Hu and Seeger, 1996, Proc Natl Acad Sci USA, 93:1060-4). Hsp70, another member of the chaperone family of proteins, is known to play a critical role in the clathrin type vesicle trafficking pathway (Newmyer et al., 2001, J. Cell. Biol., 152:607-620; Chang et al., 2002, J. Cell. Biol., 159:477-487). Hsp90 may well play an analogous role in the COPI type vesicle trafficking pathway in cells where the otoferlin cochlear isoform is expressed.

Hsp90 is a highly abundant cellular protein accounting for 2-5% of total cellular protein. Inhibition of Hsp90 activity caused selective degradation of important signaling proteins (client proteins) responsible for controlling cell proliferation, cell cycle regulation and apoptosis (Maloney et al., 2002, Expert Opin. Biol. Ther., 2:3-24). Inhibitors of Hsp90 such as geldanamycin inhibited Hsp90 activity by interfering with its intrinsic ATPase activity. Four classes of Hsp90 inhibitors are currently being studied: 1) benzoquinone ansamycins and their analogues such as herbimycin A, geldanamycin, and 17-AAG; 2) macrocyclic antibiotics such as radicicol; 3) coumarin antibiotics such as novobiocin; and 4) "rationally" designed purine-based inhibitors. These inhibitors have shown significant promise as anti-tumor drugs. Recent studies indicate that Hsp90 in tumor tissue exists in a functionally distinct form relative to non-tumor cells (Kamal et al., 2003, Nature, 425: 407-10). Tumor-activated Hsp90 has markedly higher affinity for these Hsp90 inhibitors, resulting in the dramatic ability of tumor tissue to accumulate high levels of Hsp90 inhibiting drugs. The lack of available Hsp90 results in the selective degradation of proteins essential for tumor growth.

The motifs represented in YSLPGYMVKKLLGA (SEQ ID NO:1) represent an important signaling crossroads that integrates Hsp90 regulated activity with the process of membrane repair (FIG. 7). Such fundamental processes such as cell division can be interrupted or delayed when such motifs are presented appropriately.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

Sequence Free Text

```
SEQ ID NO:1    YSLPGYMVKKLLGA     peptide
SEQ ID NO:2    CYSLPGYMVKKLLGA    peptide
SEQ ID NO:3    CYSLPGYLAKKILGA    peptide
SEQ ID NO:4    CYSLPGYMVSSLLGA    peptide
SEQ ID NO:5    CYSLPGYLASSILGA    peptide
```

What is claimed is:

1. An isolated peptide comprising the sequence YSLPGYMVKKLLGA (SEQ ID NO:1) and having no more than 30 amino acids.

2. An isolated peptide consisting of the sequence YSLPGYMVKKLLGA (SEQ ID NO:1).

3. The isolated peptide of claim 1, wherein the isolated peptide binds to at least one member of the Hsp90 class of proteins and inhibits the ability of the Hsp90 protein to regulate one or more client proteins.

4. An isolated peptide consisting of a fragment of the sequence YSLPGYMVKKLLGA (SEQ ID NO:1), wherein said fragment consists of at least 7 contiguous amino acids of SEQ ID NO:1.

5. An isolated peptide consisting of a fragment of the sequence YSLPGYMVKKLLGA (SEQ ID NO:1), wherein said fragment consists of 12 or more contiguous amino acids of SEQ ID NO:1.

6. The isolated peptide of claim 1 which binds to the N-terminal pocket of an Hsp90 protein.

7. A pharmaceutical composition comprising the peptide of claim 1 and a pharmaceutically acceptable carrier.

8. A pharmaceutical composition comprising the peptide of claim 2 and a pharmaceutically acceptable carrier.

9. A pharmaceutical composition comprising the peptide of claim 4 and a pharmaceutically acceptable carrier.

10. The isolated peptide of claim 4, wherein the isolated peptide binds to at least one member of the Hsp90 class of proteins and inhibits the ability of the Hsp90 protein to regulate one or more client proteins.

11. The isolated peptide of claim 5, wherein the isolated peptide binds to at least one member of the Hsp90 class of proteins and inhibits the ability of the Hsp90 protein to regulate one or more client proteins.

12. An isolated peptide, the peptide consisting of 14 to about 30 contiguous amino acids found in the C terminus of the human or mouse otoferlin isoform and the peptide comprises the amino acid sequence YSLPGYMVKKLLGA (SEQ ID NO: 1).

13. The isolated peptide of claim 12, wherein the isolated peptide binds to at least one member of the Hsp90 class of proteins and inhibits the ability of the Hsp90 protein to regulate one or more client proteins.

14. A pharmaceutical composition comprising the peptide of claim 5 and a pharmaceutically acceptable carrier.

15. A pharmaceutical composition comprising the peptide of claim 12 and a pharmaceutically acceptable carrier.

16. A cosmetic formulation comprising the peptide of claim 1.

17. A cosmetic formulation comprising the peptide of claim 2.

18. A cosmetic formulation comprising the peptide of claim 4.

19. A cosmetic formulation composition comprising the peptide of claim 5.

20. A cosmetic formulation comprising the peptide of claim 12.

21. An in vitro method of binding at least one member of the Hsp90 class of proteins, the method comprising contacting at least one member of the Hsp90 class of proteins in vitro with an isolated peptide of claim 1, wherein the isolated peptide of claim 1 binds to at least one member of the Hsp90 class of proteins.

22. The in vitro method of claim 21 wherein the binding of the isolated peptide of claim 1 to at least one member of the Hsp90 class of proteins inhibits the ability of the Hsp90 protein to regulate one or more client proteins.

* * * * *

UNITED STATES PATENT AND TRADEMARK OFFICE
CERTIFICATE OF CORRECTION

PATENT NO. : 7,491,701 B2  
APPLICATION NO. : 11/034404  
DATED : February 17, 2009  
INVENTOR(S) : Philip M. Kelley Page 1 of 1

It is certified that error appears in the above-identified patent and that said Letters Patent is hereby corrected as shown below:

On the title page, line 3, under FOREIGN PATENT DOCUMENTS, delete "A3 8/2005" and insert --A3 8/2006--;

On page 2, line 27, after Kamal et al., delete "cofers" and insert --confers--;

On page 2, line 52, after Miyake et al., delete "*J. Cell. Biol.*, 1996" and enter --*J. Cell. Biol.*, 1995--;

On page 3, line 36, after National Center for Biotechnology Information, National Library of Medicine, National Institutes of Health, GenBank Locus AK033317, delete "Rinken" and enter --RIKEN--;

In column 2, line 13, delete "ansarnycin-binding" and insert --ansamycin-binding--;

In column 22, line 8, delete "coatomer protein I" and insert --<u>co</u>atmer <u>p</u>rotein <u>I</u>--.

Signed and Sealed this

Twenty-first Day of July, 2009

JOHN DOLL  
*Acting Director of the United States Patent and Trademark Office*